US012672795B2

(12) United States Patent
Chen et al.

(10) Patent No.: US 12,672,795 B2
(45) Date of Patent: Jul. 7, 2026

(54) CAPTURING TRUNCATED PROTEOFORMS IN EXHALED BREATH FOR DIAGNOSIS OF TUBERCULOSIS

(71) Applicant: Zeteo Tech, Inc., Sykesville, MD (US)

(72) Inventors: Dapeng Chen, Sykesville, MD (US); Wayne A. Bryden, Sykesville, MD (US); Michael McLoughlin, Sykesville, MD (US); Kiana M. Kiser, Hanover, MD (US); Emily R. Caton, Reisterstown, MD (US); Caroline R. Haddaway, Annapolis, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 282 days.

(21) Appl. No.: 18/384,501

(22) Filed: Oct. 27, 2023

(65) Prior Publication Data

US 2024/0074673 A1 Mar. 7, 2024

Related U.S. Application Data

(63) Continuation-in-part of application No. 17/886,443, filed on Aug. 11, 2022, which is a
(Continued)

(51) Int. Cl.
*B01J 20/28* (2006.01)
*A61B 5/08* (2006.01)
(Continued)

(52) U.S. Cl.
CPC ......... *A61B 5/082* (2013.01); *B01J 20/28004* (2013.01); *B01J 20/286* (2013.01); *B01J 20/3204* (2013.01); *B01J 2220/58* (2013.01)

(58) Field of Classification Search
CPC .. G01N 33/497; A61B 5/082; B01J 20/28004; B01J 20/286; B01J 20/3204; B01J 2220/58
(Continued)

(56) References Cited

U.S. PATENT DOCUMENTS 6,062,392 A 5/2000 Birmingham et al.
6,267,016 B1 7/2001 Call et al.
(Continued)

FOREIGN PATENT DOCUMENTS

EP 3336543 A1 6/2018
EP 2823300 B1 10/2019
(Continued)

OTHER PUBLICATIONS

International Search Report and Written Opinion for PCT/US2020/048035, issued by ISA/KIPO on Dec. 30, 2020.
(Continued)

*Primary Examiner* — Peter J Macchiarolo
*Assistant Examiner* — Rodney T Frank
(74) *Attorney, Agent, or Firm* — Paradice & Li LLP; Anand S. Chellappa

(57) ABSTRACT

Methods and devices to capture and analyze aerosolized particles in exhaled air including protein biomarkers and their truncated proteoforms characteristic of tuberculosis to enable rapid detection of diseases. Methods and systems to selectively capture aerosolized particles using a packed bed column. The captured particles are eluted using one or more solvents and analyzed using devices including MALDI-TOFMS.

15 Claims, 9 Drawing Sheets

Related U.S. Application Data continuation-in-part of application No. 17/827,708, filed on May 29, 2022, which is a continuation-in-part of application No. PCT/US2022/022964, filed on Mar. 31, 2022.

(60) Provisional application No. 63/325,435, filed on Mar. 30, 2022, provisional application No. 63/249,357, filed on Sep. 28, 2021, provisional application No. 63/169,130, filed on Mar. 31, 2021.

(51) Int. Cl.
*B01J 20/286* (2006.01)
*B01J 20/32* (2006.01)

(58) Field of Classification Search
USPC ........................................................ 600/532
See application file for complete search history.

(56) References Cited

U.S. PATENT DOCUMENTS

| | | | |
|---|---|---|---|
| 7,779,840 B2 | 8/2010 | Acker et al. | |
| 8,409,870 B2 | 4/2013 | Van Wuijckhuijse et al. | |
| 8,424,523 B2 | 4/2013 | Ogilvie et al. | |
| 8,434,481 B2 | 5/2013 | Ogilvie et al. | |
| 8,434,483 B2 | 5/2013 | Patel et al. | |
| 8,944,059 B2 | 2/2015 | Mansour et al. | |
| 9,022,029 B2 | 5/2015 | Varga et al. | |
| 9,089,665 B2 | 7/2015 | Patel | |
| 9,675,773 B2 | 6/2017 | Colman et al. | |
| 10,632,276 B2 | 4/2020 | Fyfe et al. | |
| 10,926,052 B2 | 2/2021 | Colman et al. | |
| 11,135,392 B2 | 10/2021 | Oddo et al. | |
| 11,229,763 B2 | 1/2022 | Oddo et al. | |
| 11,246,506 B2 | 2/2022 | Gunneson et al. | |
| 11,359,733 B2 | 6/2022 | Oddo et al. | |
| 11,400,250 B2 | 8/2022 | Oddo et al. | |
| 11,547,322 B2 | 1/2023 | Lundin et al. | |
| 11,617,848 B2 | 4/2023 | Fyfe et al. | |
| 11,658,021 B2 | 5/2023 | Bryden et al. | |
| 11,826,512 B2 | 11/2023 | Oddo et al. | |
| 11,896,366 B2 | 2/2024 | Cardin | |
| 11,996,280 B2 | 5/2024 | McLoughlin et al. | |
| 12,091,056 B2 | 9/2024 | Ramakrishnan et al. | |
| 2003/0208132 A1 | 11/2003 | Baddour | |
| 2005/0137491 A1 | 6/2005 | Paz et al. | |
| 2007/0068811 A1 | 3/2007 | Tsukashima et al. | |
| 2008/0038207 A1 | 2/2008 | Edwards et al. | |
| 2009/0156952 A1 | 6/2009 | Hunter et al. | |
| 2012/0011918 A1 | 1/2012 | Bacal et al. | |
| 2012/0172679 A1 | 7/2012 | Logan et al. | |
| 2013/0217029 A1 | 8/2013 | Sislian et al. | |
| 2013/0327122 A1 | 12/2013 | Dutta et al. | |
| 2015/0377868 A1 | 12/2015 | Cooper et al. | |
| 2016/0020080 A1 | 1/2016 | Pyun et al. | |
| 2016/0022946 A1 | 1/2016 | Sislian et al. | |
| 2016/0231333 A1 | 8/2016 | Sutherland | |
| 2017/0035326 A1 | 2/2017 | King-Smith | |
| 2017/0119280 A1 | 5/2017 | Ahmad | |
| 2017/0299477 A1 | 10/2017 | Milton et al. | |
| 2017/0303822 A1 | 10/2017 | Allsworth et al. | |
| 2018/0246120 A1 | 8/2018 | Bryden et al. | |
| 2019/0000351 A1 | 1/2019 | Scampoli | |
| 2019/0094195 A1 | 3/2019 | Genter | |
| 2019/0282124 A1 | 9/2019 | Wu et al. | |
| 2020/0041485 A1 | 2/2020 | Funch-Nielsen | |
| 2020/0147333 A1 | 5/2020 | Stoll et al. | |
| 2020/0345266 A1 | 11/2020 | Schleich | |
| 2021/0318208 A1 | 10/2021 | Bayer et al. | |
| 2021/0321903 A1 | 10/2021 | Daniels | |
| 2021/0345956 A1 | 11/2021 | Keays et al. | |
| 2021/0386959 A1 | 12/2021 | Oddo et al. | |
| 2022/0034854 A1 | 2/2022 | Chen et al. | |
| 2022/0076783 A1 | 3/2022 | Cristescu et al. | |
| 2022/0183587 A1 | 6/2022 | Karshmer | |
| 2022/0322963 A1 | 10/2022 | Bryden et al. | |
| 2022/0370751 A1 | 11/2022 | Oddo et al. | |
| 2022/0381766 A1 | 12/2022 | Cardin | |
| 2022/0386893 A1* | 12/2022 | Chen ................ | A61B 10/0045 |
| 2023/0157573 A1 | 5/2023 | Chen et al. | |
| 2023/0172484 A1 | 6/2023 | Lundin et al. | |
| 2023/0256189 A1 | 8/2023 | Fyfe et al. | |
| 2024/0197202 A1 | 6/2024 | Andrasko et al. | |
| 2024/0423497 A1 | 12/2024 | Höjer | |

FOREIGN PATENT DOCUMENTS

| | | |
|---|---|---|
| JP | H0989863 A | 4/1997 |
| JP | H09126958 A | 5/1997 |
| JP | H10227725 A | 8/1998 |
| JP | 2006329779 A | 12/2006 |
| JP | 2011102747 A | 5/2011 |
| JP | 5848608 B2 | 1/2016 |
| JP | 2018194463 A | 12/2018 |
| JP | 2019184288 A | 10/2019 |
| JP | 2020534511 A | 11/2020 |
| KR | 1020160130229 | 11/2016 |
| WO | 2004090534 A1 | 10/2004 |
| WO | 2006012205 A2 | 2/2006 |
| WO | 2009045163 A1 | 4/2009 |
| WO | 2017197386 A1 | 11/2017 |
| WO | 2019011750 A1 | 1/2019 |
| WO | 2019145678 A1 | 8/2019 |
| WO | 2021061330 A1 | 4/2021 |
| WO | 2021201905 A1 | 10/2021 |

OTHER PUBLICATIONS

Written Opinion of ISA/KIPO for PCT/US2020/048040 issued Dec. 9, 2020.

International Preliminary Report on Patentability (with Annex) for PCT/US2020/048035, mailed Mar. 22, 2022 by IPEA/KR.

N. Ahmed, R. Babaei-Jadidi, S. K. Howell, P. J. Beisswenger & P. J. Thornalley, "Degradation products of proteins damaged by glycation, oxidation and nitration in clinical type 1 diabetes," Diabetologia 48, 1590-1603 (2005).

Dapeng Chen, Lucia Geis-Asteggiante, Fabio P. Gomes, Suzanne Ostrand-Rosenberg, and Catherine Fenselau, "Top-Down Proteomic Characterization of Truncated Proteoforms," J. Proteome Res. 2019, 18, 11, 4013-4019.

Allan Lipton, Kim Leitzel, Suhail M. Ali, Hyma V. Polimera, Vinod Nagabhairu,Eric Marks, Angelique E. Richardson, Laura Krecko, Ayesha Ali, Wolfgang Koestler, Francisco J. Esteva, Diana J. Leeming, Morten A. Karsdal, Nicholas Willumsen, "High turnover of extracellular matrix reflected by specific protein fragments measured in serum is associated with poor outcomes in two metastatic breast cancer cohorts," Intl. J. Cancer, 2018, 43 (11), 3027-3034.

Piero Parchi, Shu G. Chen, Paul Brown, Wenquan Zou, Sabina Capellari, Herbert Budka, Johannes Hainfellner, Patricio F. Reyes, Gregory T. Golden, Jean J. Hauw, D. Carleton Gajdusek, and Pierluigi Gambetti, "Different patterns of truncated prion protein fragments correlate with distinct phenotypes in P102L Gerstmann-Sträussler-Scheinker disease," Neuroscience, 95 (14), 8322-8327 (1998).

Helen Tsai, Brett S. Phinney, Gabriela Grigorean, Michelle R. Salemi, Hooman H. Rashidi, John Pepper, and Nam K. Tran, "Identification of Endogenous Peptides in Nasal Swab Transport Media used in MALDI-TOF-MS Based COVID-19 Screening," ACS Omega 2022, 7, 20, 17462-17471.

Hunt, J., "Exhaled breath condensate: An evolving tool for noninvasive evaluation of lung disease," J. Allergy Clin. Immunol. 2002; 110:28-34.

Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.

(56)           References Cited

OTHER PUBLICATIONS

J. Brennan McNeil, Ciara M. Shaver, V. Eric Kerchberger, Derek W. Russell, Brandon S. Grove, Melissa A. Warren, Nancy E. Wickersham, Lorraine B. Ware, W. Hayes McDonald, and Julie A. Bastarache, "Novel Method for Noninvasive Sampling of the Distal Airspace in Acute Respiratory Distress Syndrome," American J. Respiratory and Critical Care Medicine 197(8), Apr. 15, 2018.

Joerg Reifart, Christoph Liebetrau, Christian Troidl, Katharina Madlener and Andreas Rolf, "Noninvasive sampling of the distal airspace via HME-flter fuid is not useful to detect SARS-CoV-2 in intubated patients," Crit. Care (2021) 25:126.

B. Bake, P. Larsson, G. Ljungkvist, E. Ljungström, and A-C Olin, "Exhaled particles and small airways," Respiratory Research (2019) 20:8.

Fennelly K.P., Martyny J.W., Fulton K.E., Orme I.M., Cave D.M., et al. (2004) Cough-generated aerosols of *Mycobacterium tuberculosis*: a new method to study infectiousness. Am J Respir Crit Care Med 169: 604-609.

Dina Hashoul and Hossam Haick, "Sensors for detecting pulmonary diseases from exhaled breath," Eur. Respir. Rev. 2019; 28: 190011.

Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.

James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. Jan. 1, 2013; 47(4): 444-451.

Wood R., Morrow C., Barry C.E., III, Bryden W.A., Call C.J., Hickey A.J., et al.: Real-Time Investigation of Tuberculosis Transmission: Developing the Respiratory Aerosol Sampling Chamber (RASC). PLoS One. 2016; 11(1): e0146658.

Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).

Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

International Search Report of ISA/KIPO for PCT/US2020/048040 issued Dec. 9, 2020.

Chen et al., "A Novel System for the Comprehensive Collection of Nonvolatile Molecules from Human Exhaled Breath," Journal of Breath Research, vol. 15, No. 1, Oct. 20, 2020 (Oct. 20, 2020), p. 016001, XP09328706.

Chen et al., 'Noninvasive Proteomic Markers for Respiratory Tract Infections in Mechanically Ventilated Patients', medRxiv, Aug. 18, 2022, [retrieved on Jan. 18, 2025]. Retrieved from <URL: https://www.medrxiv.org/content/10.1101/2022.08.17.22278888v1>, pp. 3, 7, and figure 1.

International Search Report and Written Opinion of ISA/KIPO for PCT/US2024/052658 dated Feb. 6, 2025.

Khamchun et al., 'Coronin-1A serves as a serum biomarker for supportive diagnosis of *Mycobacterium tuberculosis* infection', Germs, Mar. 2023, pp. 20-31, [retrieved on Jan. 18, 2025]. Retrieved from <URL: https://pmc.ncbi.nlm.nih.gov/articles/PMC10659747>, p. 22 and table 1.

Song et al., 'Proteomic Profiling of Serum from Patients with Tuberculosis', Ann Lab Med 2014, 34(5), pp. 345-353, [retrieved on Jan. 18, 2025]. Retrieved from <URL: https://doi.org/10.3343/alm.2014.34.5.345>, pp. 347 and table 1.

Guise M T et al: "An experimental investigation of aerosol collection utilizing packed beds of silica aerogel microspheres", Journal of Non-Crystalline Solids, North-Holland Physics Publishing. Amsterdam, NL, vol. 285, No. 1-3, Jun. 1, 2001 (Jun. 1, 2001), pp. 317-322, XP004242941, ISSN: 0022-3093, DOI: 10.1016/S0022-3093(01)00473-2. (Year: 2001).

Bardet, C. et al. (Jan. 23, 2021) Early and specific targeted mass spectrometry-based identification of bacteria in endotracheal aspirates of patients suspected with ventilator-associated pneumonia. European Journal of Clinical Microbiology & Infectious diseases. vol 40, p. 1291-1301. (Year: 2021).

MaxiQuant technical note (2010): MultiQuant Software 2.0 for targeted protein/ peptide quantification,# 0921210-02. (Year: 2010).

Lopez-Sanchez, L. et al. (2017) Exhaled breath condensate biomarkers for the early diagnosis of lung cancer using proteomics. American Journal of Physiological Lung Cell Molecular Physiology, vol. 313, L664-L676. (Year: 2017).

Qu, J. et al. (2010) Proteomic expression profiling of Haemophilus influenzae grown in pooled human sputum from adults with chronic obstructive pulmonary disease reveal antioxidant and stress response. BMC Microbiology, vol. 10: 162, 12 pages. (Year: 2010).

Dupree (2020) A critical review of Bottom-up proteomics: the good, the bad and the future of this field. Proteomes, vol. 8 No. 14, 8030114, 26 pages. (Year: 2020).

Amann, A et al. (2014) Analysis of exhaled breath for disease detection. Ann Rev Anal Chem. vol. 7:435-482. (Year: 2014).

Bregy (2018) Real-time mass spectrometric identification of metabolites characteristic of chronic obstructive pulmonary disease in exhaled breath. Clinical Mass Spectrometry, vol. 7, 29-35. (Year: 2018).

Ross, M.H, et al (2019) Host-based diagnostics for acute respiratory infections. Clinical Therapeutics, vol. 41, No. 10, p. 1923-1938. (Year: 2019).

"Hsueh, M-F. (2016) Elucidating the molecular composition of cartilage by proteomics. Journal of Proteome Research, vol. 15, p. 374-388. (Year: 2016)".

Stegemann, C. (2013) Proteomic identification of matrix metalloproteinase substrates in the human vasculature. Circ Cardiovasc Genet. vol. 6, p. 106-117 (Year: 2013).

International Search Report and Written Opinion of ISA/KIPO for PCT/US2022/022964 dated Jul. 13, 2022.

International Preliminary Report on Patentability (with Annex) for PCT/US2022/022964 dated May 11, 2023 by IPEA/KR.

International Search Report and Written Opinion of ISA/KIPO for PCT/US2023/029760 dated Nov. 24, 2023.

International Preliminary Report on Patentability (with Annex) for PCT/US2023/029760 dated Oct. 8, 2024 by IPEA/KR.

"Ventilator/Ventilator Support, What to Expect," NIH, National Heart, Lung, and Blood Institute, downloaded from the internet on Jul. 8, 2024 at <https://www.nhlbi.nih.gov/health/ventilator/what-to-expect#:~:text=Ventilators>, 7—pages, last updated Mar. 24, 2022.

* cited by examiner

1313

1307
Power supply 1312
reservoir

1308
Mini
diaphragm
pump

1309
Air flow
restrictor
(1.0 L/min)

1311
CO2 sensor
module

1314
To Capture
element 1301

1310
Power adapter

CAPTURING TRUNCATED PROTEOFORMS IN EXHALED BREATH FOR DIAGNOSIS OF TUBERCULOSIS

RELATED APPLICATIONS

This patent application is a continuation-in-part of application of U.S. application Ser. No. 17/886,443, filed Aug. 11, 2022, and titled "CAPTURING TRUNCATED PROTEO-FORMS IN EXHALED BREATH FOR DIAGNOSIS AND TREATMENT OF DISEASES," which is a continuation-in-part of U.S. application Ser. No. 17/827,708, filed May 29, 2022 and titled "CAPTURING TRUNCATED PRO-TEOFORMS IN EXHALED BREATH FOR DIAGNOSIS AND TREATMENT OF DISEASES," which is a continu-ation-in-part of International Application No. PCT/US22/22964, filed Mar. 31, 2022, which is related to and claims the benefit of U.S. Provisional Appl. No. 63/169,130, filed Mar. 31, 2021, and titled "Diagnosis of Respiratory Diseases By Capturing Aerosolized Biomaterial Particles Using Packed Bed Systems and Methods," U.S. Provisional Appl. No. 63/249,357, filed Sep. 28, 2021 and titled "Diagnosis of Respiratory Diseases By Capturing Aerosolized Biomaterial Particles Using Packed Bed Systems and Methods," and U.S. Provisional Appl. No. 63/325,435, filed Mar. 30, 2022, and titled "Diagnosis of Respiratory Diseases By Capturing Aerosolized Biomaterial Particles Using Packed Bed Sys-tems and Methods," the entire disclosures of which are incorporated herein by reference.

FEDERALLY SPONSORED RESEARCH AND DEVELOPMENT

None.

FIELD

This disclosure relates to methods and devices for cap-turing and analyzing aerosolized organic biomaterials such as virus and bacteria particles and related truncated proteo-forms in exhaled breath using packed bed columns to enable rapid, low-cost detection of several diseases including respi-ratory tract diseases such as COVID-19. More particularly, but not by way of limitation, the present disclosure relates to methods and devices for analyzing truncated proteoforms and non volatile organic particles in exhaled breath to detect diseases using mass spectrometry.

BACKGROUND

Exhaled breath aerosols contain non-volatile organic bio-markers produced by human biological processes, including metabolic, immunological, and inflammatory processes, and the composition of these compounds and proteoforms may be viewed as indicators for human health. The detection of these protein biomarkers and their truncated proteoforms using analysis of exhaled breath could be used to monitor, screen, diagnose, and distinguish between healthy persons and persons with health issues such as obesity, diabetes, liver cancer, lung cancer, and the like. The capture of these biomarkers from exhaled breath and subsequent analysis could reveal health risk factors and assist with diagnosis, treatment and mitigating the spread of diseases.

Lower Respiratory Tract Infections ("LRTIs"), including pneumonia, tuberculosis and bronchitis, rank fifth in global mortality, and caused approximately 2.74 million deaths in 2015. Immediate diagnosis followed by antimicrobial intervention is crucial for LRTI management. As described below, conventional microbiological culture methods are slow, leading to diagnostic delays. Nucleic Acid Amplifica-tion Test ("NAAT")-based molecular diagnostic approaches offer rapid results but limit to differentiate between coloni-zation and infection due to their reliance on pathogen markers and are not able to determine bacterial viability. Exploring host responses has hence become crucial in enhancing the accuracy of LRTI diagnosis. Human exhaled breath contains peptides and proteins, which are potential indicators of diseases. Historically, capturing these biomo-lecules is challenging due to the limitations of exhaled breath collection technologies.

Although research has shown that respiratory diseases can be detected from breath aerosol and breath condensate, modern clinical tests for infections or diseases such as COVID-19, tuberculosis, influenza, pneumonia continue to utilize sputum, blood, or nasal swabs. Coronavirus Disease ("COVID-19") is a disease caused by the newly emerged coronavirus SARS-CoV-2. This new coronavirus is a respi-ratory virus and spreads primarily through droplets gener-ated when an infected person coughs or sneezes, or through droplets of saliva or discharge from the nose. The novel coronavirus is highly contagious and has created a pan-demic. Further, tuberculosis ("TB") has surpassed HIV/ AIDS as a global killer with more than 4000 daily deaths. (Patterson, B., et al., 2018). In communities with highly prevalent HIV, *Mycobacterium tuberculosis* (Mtb) genotyp-ing studies have found that recent transmission, rather than reactivation, accounts for the majority (54%) of incident TB cases. The physical process of TB transmission remains poorly understood and the application of new technologies to elucidate key events in infectious aerosol production, release, and inhalation, has been slow. Interruption of trans-mission would likely have a rapid, measurable impact on TB incidence. To mitigate transmission of respiratory diseases, rapid disease detection tools are needed.

The time associated with a diagnostic assay is a critical parameter for a fielded, or "point of care" test. Active Case Finding ("ACF") is an example of a fielded diagnostic assay because, by definition, ACF takes place outside the health-care system. According to the World Health Organization, ACF is a "systematic identification of people with suspected active TB, using tests, examinations, or other procedures that can applied rapidly." In the U.S., a point-of-care test needs to provide an answer in preferably 20 minutes or less. The GeneXpert assay (Cepheid, Inc., Sunnyvale, CA) may be used to provide diagnosis in about one hour. The Gen-eXpert genetic assay is based on polymerase chain reaction ("PCR") and may be used to analyze a sample for respiratory disease diagnosis. This assay is expensive to implement on a "cost per test" basis and is not widely deployed. Because of high cost, it is not used to screen patients who appear healthy (non-symptomatic) but might have TB infection in developing countries, but rather, is used to confirm a diag-nosis that is strongly suspected based on other tests or factors. The goal of ACF is to get those infected to treatment earlier, thereby reducing the average period of infection and the spread of the disease. In the case of TB, by the time an individual goes to a clinic for help, that person may have transmitted the infection to between about 10 other people and about 115 other people. ACF can help to reduce or prevent significant TB transmission. The diagnostic systems and methods such as sputum analysis and blood analysis are either not automated and autonomously operated, or not rapid. Many have expensive assays with reagents that are consumed for each analysis, and thus, do not have general utility for active case finding, particularly in developing and under-developed countries.

There is increasing interest in new diagnostic tools for diseases, including respiratory diseases, using exhaled breath. Exhaled breath contains aerosols ("EBA") and vapors and can be collected noninvasively and analyzed for characteristics to elucidate physiologic and pathologic processes in the lung. (see Hunt, 2002). EBA analysis appears to be a compelling diagnostic tool for TB detection that allows for rapid analysis, portability, and low cost because the need for expensive assays and consumables are eliminated. To capture breath for assay, exhaled air is passed through a condensing apparatus to produce an accumulation of fluid that is referred to as exhaled breath condensate ("EBC"). Although derived from water vapor, EBC has dissolved within it nonvolatile compounds, including cytokines, lipids, surfactant, ions, oxidation products, adenosine, histamine, acetylcholine, and serotonin. In addition, EBC traps potentially volatile water-soluble compounds, including ammonia, hydrogen peroxide, ethanol, and other volatile organic compounds. EBC has readily measurable pH. EBC contains aerosolized airway lining fluid and volatile compounds that provide noninvasive indications of ongoing biochemical and inflammatory activities in the lung. Rapid increase in interest in EBC has resulted from the recognition that in lung disease, EBC has measurable characteristics that can be used to differentiate between infected and healthy individuals. These assays have provided evidence of airway and lung redox deviation, acid-base status, and the degree and type of inflammation in acute and chronic asthma, chronic obstructive pulmonary disease, adult respiratory distress syndrome, occupational diseases, and cystic fibrosis. Characterized by uncertain and variable degrees of dilution, EBC may not provide precise assessment of individual solute concentrations within the native airway lining fluid. However, it can provide useful information when concentrations differ substantially between health and disease or are based on ratios of solutes found in the sample.

Patterson et al. (2018) used a respiratory aerosol sampling chamber ("RASC"), a novel apparatus designed to optimize patient-derived exhaled breath aerosol sampling, to isolate and accumulate respirable aerosol from a single patient. Environmental sampling detects the Mtb present after a period of ageing in the chamber air. 35 newly diagnosed, GeneXpert sputum-positive, TB patients were monitored during one-hour confinement in the RASC chamber, which has a volume of about 1.4 m$^3$. The GeneXpert PCR assay for TB can accept a sputum sample and provide a positive or negative result in about one hour. The chamber incorporated aerodynamic particle size detection, viable and non-viable sampling devices, real-time $CO_2$ monitoring, and cough sound-recording. Microbiological culture and droplet digital polymerase chain reaction (ddPCR) were used to detect Mtb in each of the bio-aerosol collection devices. Mtb was detected in 77% of aerosol samples and 42% of samples were positive by mycobacterial culture and 92% were positive by ddPCR. A correlation was found between cough rate and culturable bioaerosol. Mtb was detected on all viable cascade impactor stages with a peak at aerosol sizes 2.0-3.5 micron. This suggests a median of 0.09 CFU/litre of exhaled air for the aerosol culture positives and an estimated median concentration of $4.5 \times 10^7$ CFU/ml of exhaled particulate bio-aerosol. Mtb was detected in bioaerosols exhaled by a majority of the untreated TB-patients using the RASC chamber. Molecular detection was found to be more sensitive than Mtb culture on solid media. Exhaled breath analytical tools have not been commercialized for ACF because methods and devices to efficiently collect and concentrate the trace amounts of analyte present in exhaled breath are lacking. Furthermore, there is no standard or methodology to assess how much exhaled breath is sufficient for a particular diagnosis.

The lack of a non-invasive method and reliable molecular biomarkers is a significant barrier to diagnosing respiratory tract infections ("RTI") in critical care settings, especially in patients breathing using mechanical ventilators. Current diagnostic methods rely on non-specific clinical observations, such as tracheal secretions, chest X-ray findings, body temperature, white blood cell counting, oxygenation, and microbiological testing. Score systems, such as clinical pulmonary infection score ("CPIS"), have been developed based on these clinical symptoms. Although the clinical notes and score systems can be used to determine antibiotic treatment, they generally lack sensitivity and specificity for RTI diagnosis, making it challenging for clinicians to provide rational clinical decisions. Quantitative microbial culture of specimens collected from the lower respiratory tract, such as the non-invasive endotracheal aspirate ("ETA"), have been used for RTI diagnosis but are unable to inform whether the identified bacteria result from common respiratory tract colonization or from another infection. Bronchoalveolar lavage ("BAL") has been used as a high-quality specimen collection technique from the lower respiratory tract for causative diagnosis in intubated patients. However, this method is invasive and cannot be performed routinely in hospital ICUs. Due to these limitations, over 50% of patients administrated in intensive care units ("ICUs") are treated without an appropriate diagnosis. Therefore, the difficulty of obtaining samples from the site of infection and the absence of accurate diagnostic molecular biomarkers limit current diagnostic methods, pathogen identification, and management of RTI in intubated patients. There is an urgent need to develop a non-invasive method for sampling the site of infection and discovering accurate molecular biomarkers for RTI diagnosis.

Non-invasive sampling methods enable repeated sampling without causing risks in critically ill patients so that a disease trajectory can be monitored. Direct sampling from the lower respiratory tract would offer specimens that better represent the site of infection and thus provide better specificity for diagnosis. Non-invasive sampling methods would encourage patients to enroll in clinical trials that can be beneficial to therapeutic and diagnostic research. Human breath and exhaled aerosols have the promise to be used as a non-invasive source in clinical use. Organic molecules contained in human breath and exhaled aerosols may be used to develop non-invasive methods for detecting lung disease exacerbation and infections. The organic molecules in human breath include two main types: volatile organic compounds ("VOCs") and non-volatile organic compounds ("NOCs"). VOCs are gas molecules that can be emitted from non-biological sources, such as diets, plants, and home cleaning products, and thus lack specificity for biomarker use. On the contrary, NOCs are large molecules that exclusively originate from organisms, either humans or pathogens, and are more suitable to be used as surrogate biomarkers. Non-invasive sampling methods targeting NOCs have been developed for use in clinical settings. McNeil et al. report use of inline heat moisture exchanger ("HME") filters to collect proteins from patients with acute respiratory distress syndrome ("ARDS"). HME filters are a standard component installed in mechanical ventilators where exhaust air is present. It was reported that proteins could be captured on the HME filter as exhaled breath condensate emitted from lower airways. For this purpose, undiluted pulmonary edema fluid ("EF") samples were collected, and the protein profiles acquired from EF samples were used to compare with HME fluid samples. The results showed a similar protein profile between the two types of samples and suggested that HME could be a non-invasive alternative to EF for distal sampling airspace in patients with ARDS.

HME filters have their limitations. They include sponge-like materials with hygroscopic properties. It is speculated that the capture of proteins is via condensation on the sponge type materials. During condensation, Reifart et al. (2021) reported that submicron particles such as SARS-CoV-2 viruses are not efficiently collected on the filters mainly because the particles in human exhaled air are too small and less than 1 μm in size. Since the particles in human breath and exhaled aerosols are mainly composed of submicron particles, capturing these particles using the disclosed example devices and methods overcome the limitations of HME filters by collecting exhaled breath aerosol and breath condensate at high flow rate, high efficiency, and into relatively concentrated samples. Further, the disclosed example devices and methods provide for sample normalization by enabling the recording of individual $CO_2$ levels in exhaled breath.

Further, size sorting of aerosol can be incorporated to increase the signal to noise ratio for specific analytes prior to collection of the analytes. The concentrated samples may then be analyzed by several methods, but preferably, using methods that are sensitive, rapid, and highly specific to the analytes of interest. More preferably, the analysis will be rapid, and near real-time. Mass spectrometry, real-time PCR, and immunoassays have the highest potential to be sensitive, specific and nearly real-time. Sample collection methods are needed that can be coupled with fast diagnostic tools such as mass spectrometry ("MS") that is more rapid and reliable than sputum analysis and less invasive than blood analysis to provide a diagnostic assay that is fast, sensitive, specific and preferably, characterized by low cost per test. Such a system could be used for active case finding ("ACF") of respiratory tract diseases and also to monitor the status of patients who use ventilators to assist breathing in a hospital intensive care unit. To be effective, the sample collection and diagnostic system must be rapid and inexpensive on a "per diagnosis" basis. Low cost-per-test is a requirement for screening a large number of individuals to proactively prevent disease transmission to search for the few that are indeed infected. Low-cost devices and methods would also be required for point-of-care diagnosis of influenza and other pathogenic viruses because patients probably infected with a "common cold" may be infected with rhinovirus. In some cases, the respiratory infection will be driven by a bacterial or fungal microbe and may be treatable with antibiotics. In other cases, the microbe may be resistant to antibiotics, and a diagnostic method that can identify microbial resistance to antibiotics is preferable. Rapid EBA methods for distinguishing between viral and bacterial infections in the respiratory tract are desired while minimizing the occurrence of false negatives due to an insufficient sample volume. Mass spectrometry, genomics methods including PCR, and immunoassays have the highest potential to be sensitive and specific. Mass spectrometry, and in particular, MALDI time-of-flight mass spectrometry (MALDI-TOFMS), is a preferred diagnostic tool for analysis EBA and EBC samples because it has been demonstrated to be sensitive, specific and near real-time.

BRIEF DISCLOSURE

In some implementations, a method for detecting tuberculosis (TB) using exhaled air may include capturing truncated proteoforms in the exhaled air aerosol produced by a patient using a sample capture element including a packed bed column, wherein exhaled air is drawn into the sample capture element using a pump at a predetermined flow rate, extracting the truncated proteoforms from the packed bed column into one or more collected liquid samples including the truncated proteoforms, analyzing the one or more collected liquid samples using MALDI-TOFMS, and detecting the presence of TB if the truncated proteoforms includes one or more of interleukin-10 receptor subunit alpha (IL10RA), protein phosphatase 1 regulatory subunit 17 (PPR17), collagen alpha-1(II) chain (COL2A1), collagen alpha-1(III) chain (COL3A1), or complement component C6 (C6).

In some implementations, a capture efficiency of the sample capture element for truncated proteoforms in exhaled air is greater than 99%. In some implementations, the packed bed column may include one or more of resin beads having C18 functional groups on the surface, cellulose beads having sulfate ester functional groups on the surface, or mixtures thereof. In some other implementations, the packed bed column may include solid particles including one or more of resins, cellulose, silica, agarose, or hydrated $Fe_3O_4$ nanoparticles. In some aspects, the resin beads and cellulose beads may have a nominal diameter of at least about 20 μm. In some aspects, the resin beads and cellulose beads may have a nominal diameter of between about 40 μm and about 150 μm.

In some implementations, extracting the truncated proteoforms may include flushing the packed bed column with one or more solvents and collecting the solvent including truncated proteoforms from the packed bed. In some aspects, the one or more solvents may include one or more of acetonitrile, methanol, trifluoro acetic acid (TFA), or isopropanol (IPA), the remaining being water. In some other aspects, the one or more solvents may include between about 50 vol.-% and about 70 vol.-% acetonitrile in water, between about 50 vol.-% and about 70 vol.-% isopropanol in water, or between about 0.05 vol.-% TFA in water.

In some implementations, the sample capture element may be removably connected to an exhaled air tubing of a ventilator assisting the breathing of an intubated patient. In some aspects, the predetermined flow rate drawn through the packed bed column using the pump is between about 200 ml/min and about 3 L/min.

In some implementations, the sample capture element may be removably connected to a breath collection element configured to receive an individual's face, wherein the breath collection element forms a tight-fit with the individual's face. In some implementations, the breath collection element includes one or more of a CPR rescue mask, a CPAP mask, or a ventilator mask. In some aspects, the predetermined flow rate drawn through the packed bed column using the pump may be between about 200 ml/min and about 600 ml/min. In some implementations, the sample capture element may be removably connected to a port disposed in the breath collection element proximate to the individual's chin when the breath collection element is positioned on the individual's face without any interconnecting tubing.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIGS. 1A-B show (A) a schematic diagram of an example exhaled air aerosol collection system for use with a ventilator connected to patients diagnosed with a respiratory tract infection (RTI) in intensive care units and (B) a schematic diagram of an example subsystem configured to operate the exhaled breath aerosol sample capture system connected to the ventilator, according to some implementations.

FIG. 2 shows a schematic diagram of an example diagnostic system for respiratory diseases including an example exhaled air sample collection system, according to some implementations.

FIGS. 3A-D show (A) a Box and Whisker Plot for distinguishing between RTI patients and non-RTI patients using a class of 263 truncated proteoforms identified using mass spectrometry analysis of exhaled breath aerosols, (B) a distribution of feature ranking scores and fold-changes of six statistically significant truncated proteoforms (volcano plot) to distinguish between RTI patient and non-RTI patients based on the ion intensities of six truncated proteoforms, (C) a Box and Whisker Plot for distinguishing between RTI patients and non-RTI patients using a select class of six truncated proteoforms identified using mass spectrometry analysis of exhaled breath aerosols, and (D) an estimation of reference threshold mass spectra intensity values ($\log_{10}$) for each of the three statistically significant truncated proteoforms from their respective ROC curves (a-c), according to some implementations.

FIG. 4 shows a schematic diagram of an example method for predicting RTI from mass spectra of exhaled breath aerosol samples collected from patients using an example exhaled air aerosol sample capture elements and collection system, according to some implementations.

FIGS. 5A-C show (A) a plot showing the relationship between composite score estimated for the three statistically significant truncated proteoforms and probability of distinguishing between RTI and non-RTI (RTI prediction accuracy), (B) ROC curves with AUC values for each of the three truncated proteoforms, and (C) a ROC curve with AUC value for a general linear model using the selected subset (three proteoforms) of the class of the six truncated proteoforms, according to some implementations.

Figure 1A:
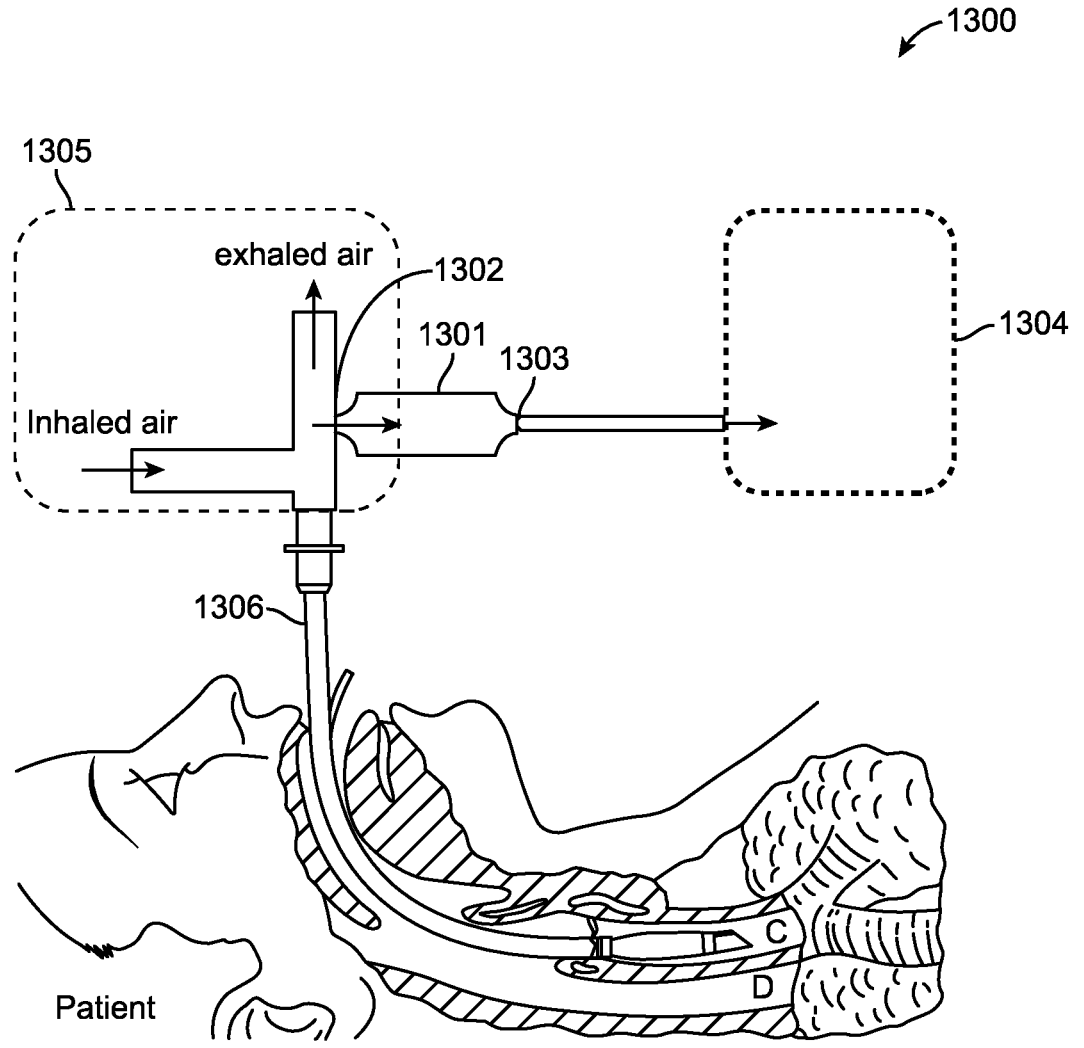

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this disclosure, aerosol generally means a suspension of particles dispersed in air or gas. "Autonomous" diagnostic systems and methods mean generating a diagnostic test result "with no or minimal intervention by a medical professional." The U.S. FDA classifies medical devices based on the risks associated with the device and by evaluating the amount of regulation that provides a reasonable assurance of the device's safety and effectiveness. Devices are classified into one of three regulatory classes: class I, class II, or class III. Class I includes devices with the lowest risk and Class III includes those with the greatest risk. All classes of devices as subject to General Controls. General Controls are the baseline requirements of the Food, Drug and Cosmetic (FD&C) Act that apply to all medical devices. In vitro diagnostic products are those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body. The example devices disclosed herein can operate and produce a high-confidence result autonomously, and consequently, has the potential to be regulated as a Class I device. In some regions of the world with high burdens of TB infection, access to medically trained personnel is very limited. An autonomous diagnostic system is preferred to one that is not autonomous.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified." Unless otherwise specified, the concentration of chemicals, solvents and the like disclosed as a percentage refers to vol.-%.

DETAILED DISCLOSURE

Breath aerosol particles contain a variety of nonvolatile organic biomolecules such as metabolites, lipids, and proteins. The aerosol particles in exhaled breath may include one or more of microbes, viruses, metabolite biomarkers, lipid biomarkers, or proteomic biomarkers, for example, truncated proteoforms, which are characteristic of respiratory diseases and other diseases. Further, these nonvolatile molecules have a wide particle size distribution ranging from a sub-micron size to about 10 microns in size. Breath collection and disease diagnostic systems and methods that can efficiently capture different types of nonvolatile molecules of different particle sizes from exhaled breath are required. Particular aspects of the invention are described below in considerable detail for the purpose for illustrating the compositions, and principles, and operations of the disclosed methods and systems. However, various modifications may be made, and the scope of the invention is not limited to the example aspects described. Disclosed are example non-invasive methods for distinguishing between RTI and non-RTI patients by capturing truncated proteoforms contained in exhaled breath aerosols from intubated patients.

Disclosed is an example system 1300 (FIG. 1A) and method for capturing exhaled air aerosols by disposing example sample capture element 1301 including a packed bed column in fluid communication with ventilator 1305. Ventilator 1305 is a life support machine and is used in intensive care units for patients who cannot breathe on their own. For example, patients with severe symptoms of COVID-19 may need the assistance of a ventilator to breathe. A tube 1306 is inserted through the patient's mouth or nose directly into the trachea. The ventilator pushes air into the lungs through this tube and forces the person to inhale. The ventilator typically forces air in for one second, pauses for about three seconds to allow the patient to exhale through the same tube, and then repeats the cycle. Inlet end 1302 of capture element 1301 is removably connected and preferably directly to the exhaled air tubing of the ventilator to minimize particle loss. Outlet end 1303 may be removably connected to pump 1308 in subsystem 1304 (details shown in subsystem 1313) using a tubing to draw in exhaled air through the packed bed column in element 1301 at a flow rate of between about 200 ml/min and about 2.5 L/min. System 1300 may include a trap disposed between end 1303 and subsystem 1313 to collect any condensate. The trap may be cooled to a temperature below ambient temperature. An optional HEPA filter and a needle valve or flow meter may be installed between the trap and the pump. $CO_2$ in exhaled breath passes through the packed bed column. To determine if exhaled breath sample volume is adequate, a $CO_2$ sensor may be disposed between the outlet end 1303 and the trap. $CO_2$ monitoring allows for an approximation of the exhaled air volume. A particle counter may also be installed upstream of capture element 1301 and also between outlet end 1303 and the trap to detect the size and number for particles exiting the packed bed column, which may also be used to detect saturation of the bed and breakthrough of nonvolatile organic molecules from the column bed.

In some implementations, sample capture element 1301 may include a packed bed column to selectively captures breath aerosol non-volatile particles. Capture element 1301 may be disposed to be in fluid communication with system 1313 (FIG. 1B) through port 1314, which may include a quick connect/disconnect coupling. A portion of exhaled air drawn through capture element 1301 using pump 1308 may be routed to reservoir 1312 which is fluidly connected with $CO_2$ sensor 1311. Reservoir 1312 may be a well-sealed container and is used to prevent any air leaks from the $CO_2$ sensor. System 1313 may include a user interface and an on-off switch to initiate and stop sampling of exhaled breath using element 1301. Additionally, components such as flow controllers, and flow restrictors 1309 may also be packaged in portable subsystem 1313. Subsystem 1304 may include a diaphragm pump, such as a mini diaphragm pump 1308. Portable system 1313 may be 11 in.×7.5 in.×5.5 in. (L×D× H) and may include noise cancelling materials such as foam pads to reduce the noise level caused by the pump to less than 45 dB. System 1313 may be disposed at a distance from the sample capture element, for example, outside an intensive care unit in a hospital.

In some implementations, the example packed bed column in capture element 1301 may include Hamilton PRP-C18 resin beads as supplied by Sigma Aldrich and other vendors. The bed may be held in place between two porous filter plates such as frit discs. For example, a polyethylene disc having an average pore size of above 35 μm may be placed upstream of the bed and a polyethylene disc having an average pore size of 10 μm (Boca Scientific, Dedham, MA) may be placed downstream of the bed. The 35 μm frit disc allows a faster air flow rate while the smaller 10 μm frit disc traps all the C18 resin well. In an example element 1301, the packed bed may include about 25 mg of C18 resin beads having a nominal diameter between about 12 μm and about 20 μm. Non-volatile organic components in exhaled breath removably interact with the C18 functional groups on the beads and are trapped. Water, volatiles and other hydrophilic molecules pass through the bed and may be trapped in glass trap.

In some implementations, besides C18 functional groups, other functional groups that show affinity to nonvolatile molecules may be used as adsorbents in the column immobilized on solid phase beads such as resin beads. The solid phase beads may be made of polymers and particles such as resins, cellulose, silica, agarose, and hydrated $Fe_3O_4$ nanoparticles. Adsorbent materials may include other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also include one or more of ion exchange phases, polymer phases, antibodies, glycans, lipids, DNA or RNA. For capturing aerosolized virus particles, example sample capture element 1301 may include sulfate ester-immobilized cellulose beads. Alternately, sample capture element 1301 may include packed beds of C18 beads and sulfate ester-immobilized cellulose beads. Alternately, sample capture element 1301 may include a packed bed of a mixture of C18 beads a sulfate ester-immobilized cellulose beads. Example sulfate beads may include Cellufine Sulfate beads (JKC Corp., Japan). Particle diameter may be between about 40 μm and about 130 μm. An example sample capture element may include about 100 mg of sulfate ester-immobilized cellulose beads disposed as a packed bed column. The example sample capture element may have an internal diameter of about 7 mm and length of about 30 mm.

Figure 1B:
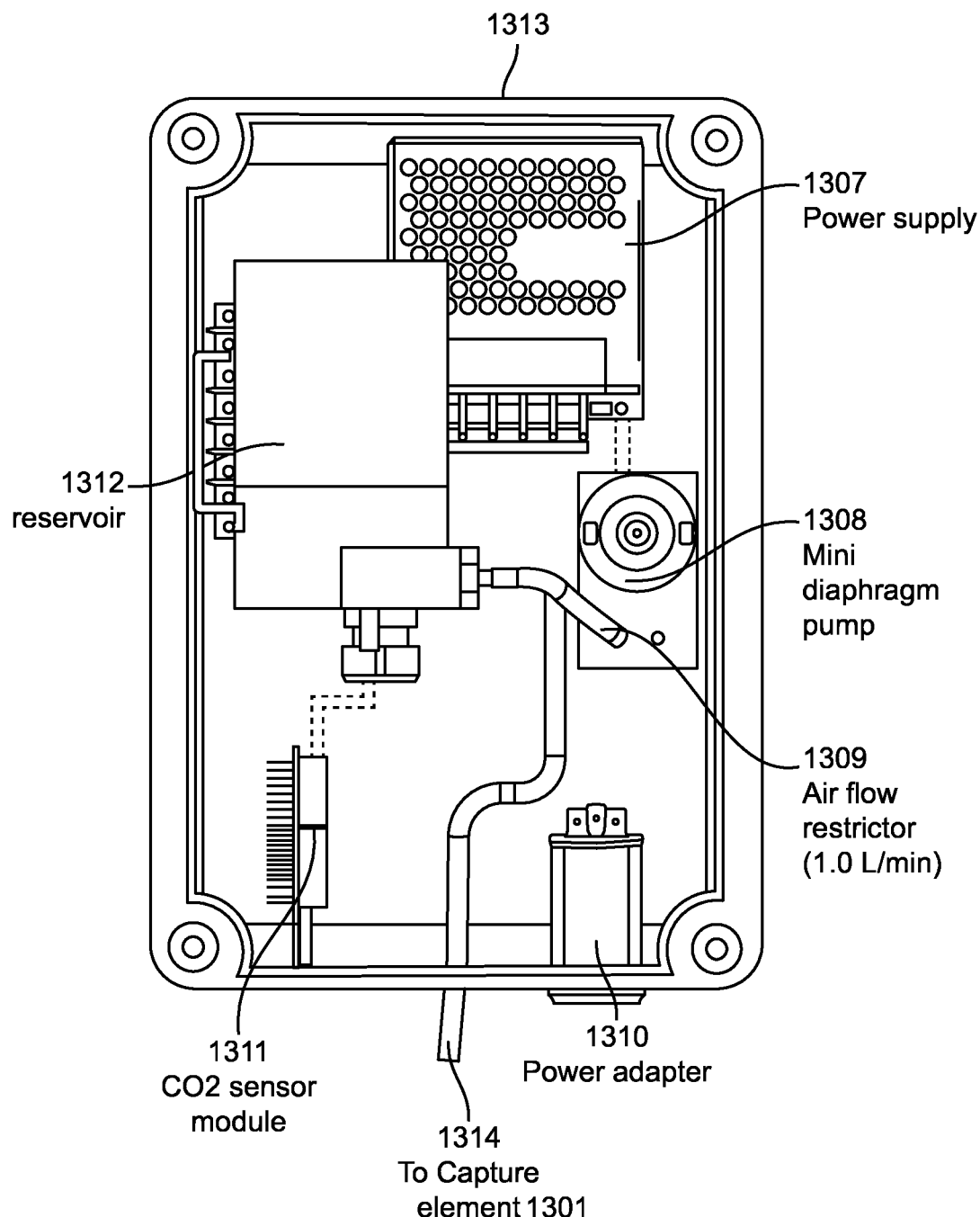

In some implementations, the capacity of the C18 beads in element 1301 to capture non-volatile organic molecules may be between about 0.05 mg (non-volatile organics)/mg beads and about 0.5 mg/mg. The capacity of C18-bonded resin beads in the column bed in example capture element may be about 0.1 mg/mg. That is, a column bed having 25 mg C18 beads would be expected to be characterized by a capacity to trap or adsorb about 2.5 mg of non-volatile organic molecules. Pump 1308 may be a diaphragm pump. Data from the $CO_2$ sensor may be recorded on a non-volatile memory card such as an SD card that is commonly used in portable devices. A flow rate sensor may be installed to monitor the flow rate through the C18 packed bed column. Alternately, a flow controller may be employed to achieve a consistent flow rate, for example, a flow rate of 500 mL/min through the packed bed column. To enable exhaled breath aerosol sampling from a ventilator disposed in hospital intensive care units using example capture element 1301, pump 1308 may be packaged along with a $CO_2$ sensor 1311, associated power supply 1307, system control components, and required fluidic components (tubings, quick connect/disconnect couplings at the like) into a portable system 1313 (FIG. 1B).

Figure 2:
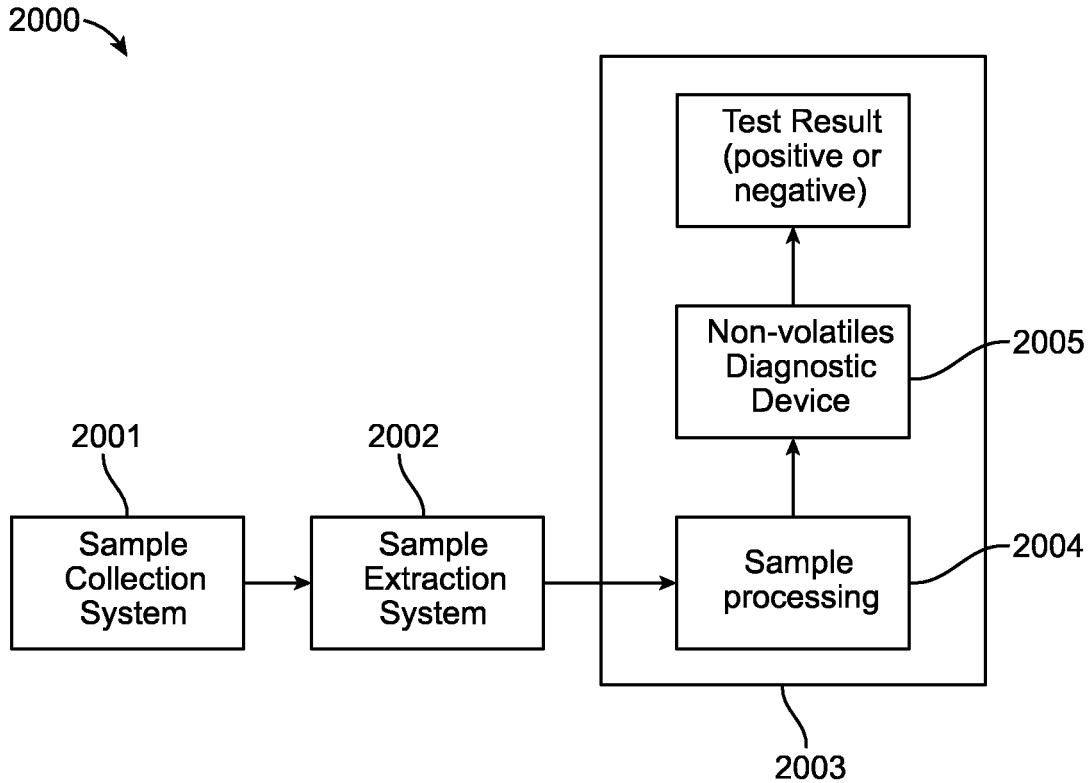

Disclosed is an example diagnosis system 2000 (FIG. 2), which may include a breath sample collection system 2001 disposed in fluid communication with a sample extraction system 2002 and an analysis system 2003. The sample collection system 2001 may include example collection system 1301 as described above. After a predetermined sample collection period, sample capture element 1301 may be removed from system 1300. Element 1301 may then be autoclaved at 110° C. for about 10 minutes to disinfect element 1301 prior to extracting the captured aerosol particles. Captured non-volatile aerosol particles may be extracted by washing (or flushing) the column with about 200 μL to about 400 μL of a solvent including one or more of 70% acetonitrile (ACN), about 50% to about 70% methanol, or about 50% to about 70% isopropyl alcohol (IPA). For example, 50% ACN flush may be used to elute metabolites and proteins in a first-stage flush followed by 70% IPA flush to elute lipids from the packed bed column.

In some implementations, the organic solvent may be removed, if needed, from the packed bed column by lyophilization overnight to preserve the captured bioaerosol particles. The organic solvent may be also removed by incubating on a heating block at about 70° C. for about 30 minutes. Finally, the bed may be washed with about 0.05% TFA (trifluroacetic acid). The sample extraction system may be used to extract the trapped non-volatile organics from the packed bed column in system 1300 and may be disposed in-line or off-line in system. When system 2002 is disposed off-line, at the conclusion of exhaled breath sample collection, capture element 1301 may be removed from system 1300 and eluted with an organic solvent in extraction system 2002 to remove non-volatile organics from the packed bed column.

In some implementations, example organic solvents include, but are not limited to, about 50-70% acetonitrile in water to extract trapped non-volatile organics (strongly polar non-volatile organic molecules, proteins and the like) from the packed bed column. The extraction may be repeated using the same or another solvent, that includes, but is not limited to 50-70% isopropanol in water to extract less polar lipid molecules from the packed bed. Other organic solvents include between about 50% and about 70% methanol in water, and about 50% methanol in about 50% chloroform. When system 2002 is disposed in-line, one or more of a $CO_2$ sensor or a particle counter may be disposed upstream of extraction system 2002. System 2002 may include a solvent vessel, a pump to transfer the solvent from the solvent to packed bed column, and a vessel to collect the solvent including the non-volatile biomarkers into another vessel or cup. Alternately, system 2002 may include an injector to inject solvent into the packed bed column and collect the extract liquid including non-volatile organics and biomarkers in a suitable cup or vessel, or other laboratory tubes having a small volume. The captured sample in solvent may be further processed and analyzed in analysis system 2003.

Many diagnostic devices may be adapted for use in analysis system 2003 that include, but are not limited to, devices that perform genomics-based assays (such as PCR, rt-PCR and whole genome sequencing), biomarker recognition assays (such as ELISA), and spectral analysis such as mass spectrometry (MS). In some implementations, of these diagnostic devices, MS is preferable on account of its speed of analysis. The MS techniques that are preferable for biomarker identification are electrospray ionization (ESI) and matrix assisted laser desorption ionization (MALDI) time of flight MS (TOFMS). ESI may be coupled to high resolution mass spectrometers. MALDI-TOFMS devices may be compact, lightweight, consume less than 100 watts of power and provide sample analysis in less than 15 minutes. MALDI-TOFMS is a preferred diagnostic device for point-of-care diagnostics suitable for ACF. The sample must be dry before it is inserted into the vacuum chamber of the MS and subjected to laser pulses from an ultraviolet laser. This interaction between the sample and the laser creates large, informative biological ion clusters that are characteristic of the biological material. When a concentrated sample is provided by sample processing system 2004 including only trace levels of water or trace levels organic solvents such as 50% to 70% of one of acetonitrile, methanol, and isopropanol in water, sample analysis using MS may take less than 5 minutes (including the sample preparation) because less time is needed to evaporate the water from the sample.

MALDI-TOFMS may be used to identify live/active agents that include, but are not limited to, *B. anthracis* spores (multiple strains), *Y. pestis, F. tularensis*, Venezuelan equine encephalitis virus (VEE), Western equine encephalomyelitis virus (WEE), Eastern equine encephalitis virus (EEE), botulinum neurotoxins (BoNT), *staphylococcus* Enterotoxin (SEA), Staphylococcal enterotoxin B (SEB), ricin, abrin, Ebola Zaire strain, aflatoxins, saxitoxin, conotoxins, Enterobacteria phage T2 (T2), HT-2 toxins (HT2), cobra toxin, biothreat simulants including *B. globigii* spores, *B. cereus* spores, *B. thuringiensis* Al Hakam spores, *B. anthracis* Sterne spores, *Y. enterocolitica, E. coli*, MS2 virus, T2 virus, Adenovirus and nonvolatile biochemical threats including NGAs (nonvolatile), bradykinin, oxytocin, Substance P, angiotensin, diazepam, cocaine, heroin, and fentanyl. Further, the example systems and methods disclosed herein may be used to achieve accurate detection and identification of SARS-CoV-2 from human breath samples.

In "matrix assisted laser desorption ionization" (MALDI), the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field. Microbiology and proteomics have become major application areas for mass spectrometry; examples include the identification of bacteria, discovering chemical structures, and deriving protein functions. MALDI-MS has also been used for lipid profiling of algae. During MALDI-MS, a liquid, which usually includes an acid, such as trifluoroacetic acid (TFA), and a MALDI matrix chemical such as alpha-cyano-4-hydroxycinnamic acid, is dissolved in a solvent and added to the sample. Solvents include acetonitrile, water, ethanol, and acetone. TFA is normally added to suppress the influence of salt impurities on the mass spectrum of the sample. Water enables hydrophilic proteins to dissolve, and acetonitrile enables the hydrophobic proteins to dissolve. The MALDI matrix solution is spotted on to the sample on a MALDI plate to yield a uniform homogenous layer of MALDI matrix material on the sample. The solvents vaporize, leaving only the recrystallized matrix with the sample spread through the matrix crystals. The acid partially degrades the cell membrane of the sample making the proteins available for ionization and analysis in an MS. Other MALDI matrix materials include 3,5-dimethoxy-4-hydroxycinnamic acid (sinapinic acid), $\alpha$-cyano-4-hydroxycinnamic acid ($\alpha$-cyano or $\alpha$-matrix) and 2,5-dihydroxybenzoic acid (DHB) as described in U.S. Pat. No. 8,409,870.

The analytical methods for the analysis of metabolites, proteins, and lipids may include silver staining for protein profiling, protein assay for protein content, bottom-up proteomics and LC-MS/MS for metabolomics and lipid-omics, and MALDI-TOF mass spectrometry for molecule profiling. In an example test, exhaled breath aerosol from patients infected with pneumonia were collected using capture element 1301 connected to a ventilator. During subsequent analysis, protein content measured using protein assay and molecule profiling measured using MALDI-TOF MS were found to be good indicators of pneumonia infection in patients as revealed by Pearson's correlation heatmap including the variables of collected total exhaled air volume, $CO_2$ content in exhaled air, protein content, MALDI-TOF total ion intensity and MALDI-TOF MS single peak (4820 m/z) intensity.

In some implementations, analysis system 2003 may include sample processing system 2004 and one or more diagnostic device 2005. Sample processing system 2004 may include elements necessary to perform one or more of the following steps:

(a) Placing the sample in at least one of a cup, a vial and a sample plate. For example, the Series 110A Spot Sampler (Aerosol Devices) uses 32 well plates with circular well shape (75 µL well volume) or teardrop well shape (120 µL well volume) which are heated to evaporate the solvent and excess fluid/liquid in the sample to concentrate the sample;

(b) Placing the sample in a cup and exposed to a source of vacuum or freeze-drying device to cause the solvent to evaporate to concentrate the sample; and, (c) hot digestion of proteins and virus particles. The samples may be centrifuged to remove chemical contamination particles.

Virus (e.g., SARS-CoV-2) detection is centered on detection of viral proteins, which is a difficult challenge. An example method for virus detection may include glycan-based capture matrix (beads) to pull the target virus out of the background matrix (e.g., other non-virus biomolecule, contaminants). An aliquot of the sample collected using sample collection system 1300 may include other background contaminants and may be applied to a bead carrying the capture probe. One or more of glycan, heparin, or carbohydrates may be used as capture materials or probes bound on resin beads or similar types of beads. An optional washing step may be used to remove any nontargeted-virus contaminants. The concentrated and purified virus may be eluted off the beads using suitable solvents into a sealed heating chamber containing an organic acid which may include formic acid or acetic acid and heated to 120° C. for about 10 minutes to digest the proteinaceous toxin down into specific peptide fragments. This hot acid protein digestion protocol cleaves the protein at aspartic acid residues creating a highly reproducible peptide pattern.

In some implementations, the capture and digestion processes described may be accomplished with antibodies and enzyme, respectively. Using this example sample processing for MALDI-TOFMS, sensitivity for ricin biotoxin of better than 100 ng/mL (with S/N of about 50:1) in clean buffer was achieved. At S/N (signal to noise ratio) of 3:1, limits of detection (LOD) of <10 ng/mL may be achieved. For the 1 µL samples used in the MALDI-TOFMS analytical systems, about 10 ng/mL LOD equates to a total mass of about 10 µg ($10^{-12}$ g) on the probe, which is equivalent to about 20,000 viral particles. An example microfluidic sample processing system to implement the method disclosed above may be configured to analyze samples collected from the air or from other sources such as nasal swabs. The glycan-based capture column and other microfluidics components may be reusable. Large fluid reservoirs containing buffer, weak acids, and alcohols may be employed to provide sufficient capacity to measure 100's of samples in one channel of the system. Multiple systems may be run in parallel to process multiple samples simultaneously. Since no fragile and expensive biomolecular reagents are required, the system is cost effective.

Hot acid digestion cleaves the proteins reproducibly at aspartic acid residues creating known peptide sequences with known masses. These peptide mass distributions are characteristic of the progenitor proteins. Thus, digestion provides outstanding specificity if the proteins of interest are largely separated from background materials. Furthermore, the peptide mass distribution is directly determined by the genome, accounting for post-translational modifications. As soon as a new virus is isolated, it is rapidly sequenced. The RNA sequence of the SARS-CoV-2 virus may be used to accurately predict the protein sequences with modern bioinformatics tools (ExPASy bioinformatics portal). These proteins can then be "digested" in silico using bioinformatics tools to create a theoretical peptide map. Thus, the peptides that arise from SARS-COV-2 digestion can be predicted and compared to experimental data to generate a specific MALDI TOFMS signature of the organism. Reports suggest that the predominant proteins in SARS-CoV are characterized by about 46 kDa nucleocapsid protein and the 139 kDa spike proteins. Other proteins in reasonable abundance are E, M and N proteins.

Detection specificity of a target virus will require some level of background removal, particularly if the background contains other proteins. If large amounts of exogenous proteins are present, the peptide map could be dominated by non-target peptides. As previously described, affinity capture probes for the virus toxins based on glycan-decorated agarose beads may be used to readily clean up the toxins, even in large excess of background proteins, and other biomolecules. When analyzing exhaled breath for virus targets such as SARS-CoV-2, other human proteins in breath may interfere with detection specificity. An affinity-based cleanup of the sample is required to ensure highest specificity. Virus detection may require bead materials that provide more selective affinity compared to the glycan-decorated beads previously described. For example, dextran-based adsorbents may be used for purifying viruses, including coronaviruses, but the affinity of this resin for the target virus may not be satisfactory.

As an alternative, carbohydrates may be used for viral and protein purification including target viruses such as SARS-CoV and SARS-CoV-2. Further heparin, and heparan sulfate may be used as binding agents bound to resin beads. Heparin covalently linked to sepharose beads (GE Healthcare Life Sciences, Heparin Sepharose 6 Fast Flow affinity resin Product #17099801) may be used instead of glycan capture beads. This resin may enable bead-based capture affinity capture system for collecting virus particles from exhaled breath. In an example diagnostic system, exhaled breath samples may be pulled through a capture bed in a sample collection system 1300, collecting particles from the breath of patient. The resin beads (bed) may be washed to remove any background material. The viral particles adsorbed to the beads would then be eluted off using high concentration of acid solution, such as one or more of about 12.5% acetic acid, about 5% TFA, about 5% formic acid or about 10% HCl, into the hot acid digestion chamber to generate the characteristic peptides. The peptide samples may be mixed with MALDI matrix and deposited onto as suitable substrate for MALDI TOFMS analysis. The samples may also be deposited on a suitable substrate or disk that is precoated with MALDI matrix.

Reports suggests that analysis of nose and throat swabs from influenza patients and COVID-19 patients produce viral counts of between about $10^3$ and $10^{10}$ viral particles. Less is known about the viral particles count in the breath of patients. Other reports suggest that influenza patients exhaled >$10^4$ particles in about 30 minutes of breathing. If the output of SARS-CoV-2 is similar to that of influenza, an output of $10^3$ to $10^4$ particles in exhaled breath with a particle collection efficiency of >99.9% should be sufficient to identify the target virus particles in exhaled breath using the example methods and systems disclosed herein. Detection time using the example systems and methods may be between about 10 minutes and 20 minutes include the steps of sample extraction (breathing maneuvers), sample collection, sample processing (digestion) and analysis using a MALDI TOF-MS. This detection time is quite rapid compared to existing detection systems.

In some implementations, an example sample processing component may include a hot acid digestion module or cartridge to autonomously extract sample from the packed bed column 1301, perform sample clean-up, conduct the hot acid digestion and provide a sample ready for plating on a MALDI-TOFS sample substrate or disk. The cartridge may be designed for reusability by adding the capability to flush the cartridge between uses.

In the example systems and methods described herein, the packed bed column length (L) in sample capture element 1301 is about 3 mm. The nominal internal diameter of the tube is about 7 mm (D). An example packed bed including about 25 mg of C18 resin beads having a nominal particle diameter ($D_p$) of between about 12 µm and 20 µm, yields a $L/D_p$ ratio of between about 150 and 250 at a $D/D_p$ ratio of about 350 to about 580. These column parameters were found to prevent undesirable localized flow distributions in the bed to ensure that substantially all resin beads were exposed to the aerosol flow through the bed.

The disclosed example systems and methods may be used to establish a baseline of protein, metabolite, and lipids signatures in exhaled breath, which may then be used during to differentiate between the exhaled breath of patients with various diseases and offer a powerful diagnostic tool for disease detection based on the analysis of non-volatile aerosols in exhaled breath.

In some implementations, the disclosed example systems and methods may also be used for detection, monitoring and treatment of diseases other than respiratory diseases and infectious diseases. Chen et al. (2019) describe a top-down proteomic strategy for the global identification of truncated proteins without the use of chemical derivatization, enzymatic manipulation, immunoprecipitation, or other enrichment. More than 1000 truncated proteoforms were identified. Tsai et al. (2022) describe mass spectrometry based diagnostic detection of the novel coronavirus infectious disease (COVID-19) as a useful alternative to classical PCR based diagnostics. Nanoscale liquid chromatography tandem MS was used to identify endogenous peptides found in nasal swab saline transport media to identify endogenous peptides and endogenous protease cut sites. They report that SARS-CoV-2 viral peptides were not readily detected and are highly unlikely to be responsible for the accuracy of MALDI based SARS-CoV-2 diagnostics.

Lipton et al. (2018) evaluated the association of specific collagen fragments measured in serum in two independent metastatic breast cancer cohorts and report that collagen fragments quantified in pretreatment serum was associated with shorter time-to-progression and overall survival in the two independent cohorts receiving systemic therapy. Ahmed et al. (2005) measured protein glycation, oxidation and nitration adducts released by cellular proteolysis using LC-MS/MS to quantify increased protein damage and flux of proteolytic degradation products in blood and urine samples of Type 1 diabetic patients. Parchi et al. (1998) examined genomic DNA isolated from frozen tissue from the cerebral cortex, basal ganglia, and cerebellum of patients using SDS-Page electrophoresis and MALDI TOFMS and found that different patterns of truncated prion protein fragments correlated with distinct phenotypes in P102L Gerstmann-Sträussler-Scheinker disease.

Disclosed is an example method 400 (FIG. 4) for predicting a respiratory tract infection (RTI) in intubated patients and other diseases in patients. Clinical trials baseline data may be obtained for diagnosing the presence or absence of the RTI by culturing one or more of sputum samples, endotracheal tube samples (ET), or bronchoalveolar lavage (BAL) for each patient in a group of patients with and without the RTI. In step 401, truncated proteoforms in mass spectra of exhaled breath aerosols may be identified. As previously discussed, exhaled breath aerosols may be selectively captured using a packed bed column and extracted into one or more liquid collected samples. The one or more liquid samples may be analyzed using mass spectrometry to obtain raw mass spectra. In step 402, a class of statistically significant truncated proteoforms characteristic of a respiratory tract infection are identified using mass spectra feature selection including one or more of SAM (Significance Analysis of Microarray) 403 or t-test 404. p values may be adjusted using the Benjamini-Hochberg method in step 405. In step 406, multiple logistic regression methods may be used to analyze the class of statistically significant truncated proteoforms and clinical parameters including one or more of age, gender, race, ethnicity, primary diagnosis, medication, sample collection time, microorganism identification information, white blood cell count, body temperature, fraction of inspired oxygen (FiO2) content, pulmonary radiography, or the truncated proteoforms in the class and downselect a statistically significant subset of the class of truncated proteoforms identified in step 402.

In some implementations, the presence of RTI may be predicted using at least one of calculating a composite score in step 407 representative of the statistically significant subset of the truncated proteoforms and calculating the area under the curve (AUC) of the receiver operating characteristic curve (ROC) in step 410 representative of the statistically significant subset of the truncated proteoforms in the samples.

Figure 3C:
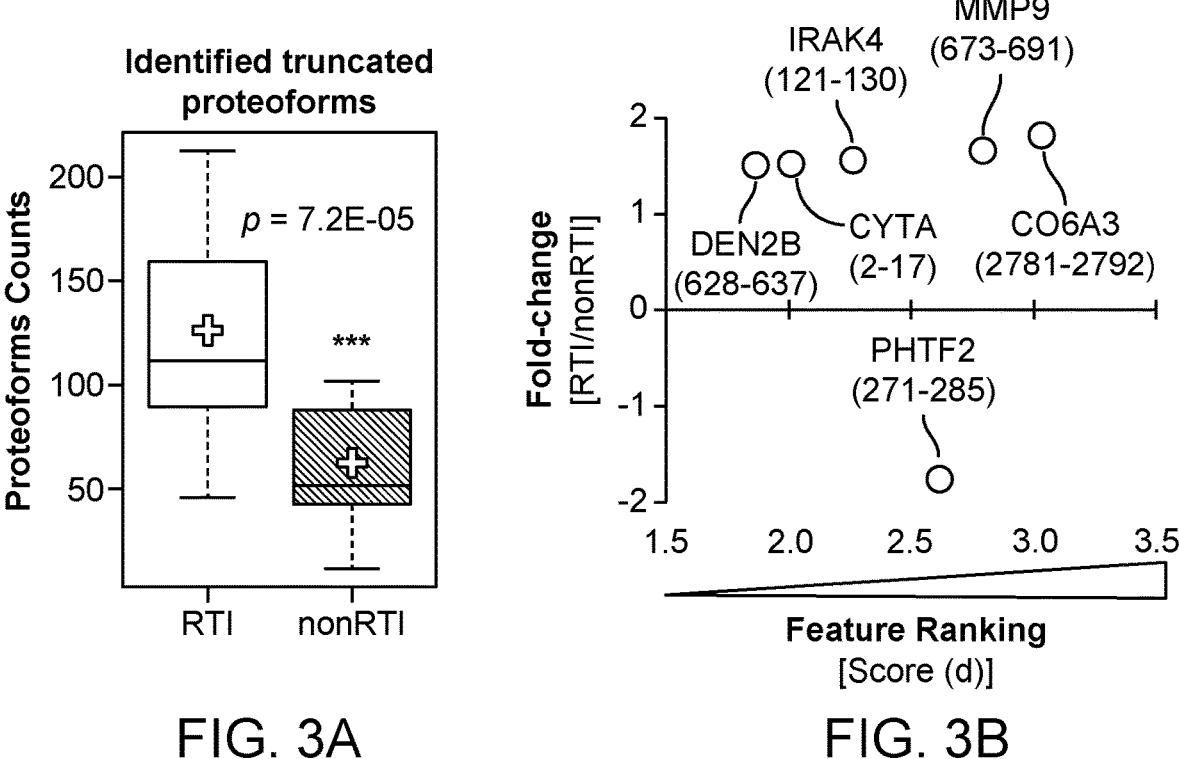
Figure 3C:
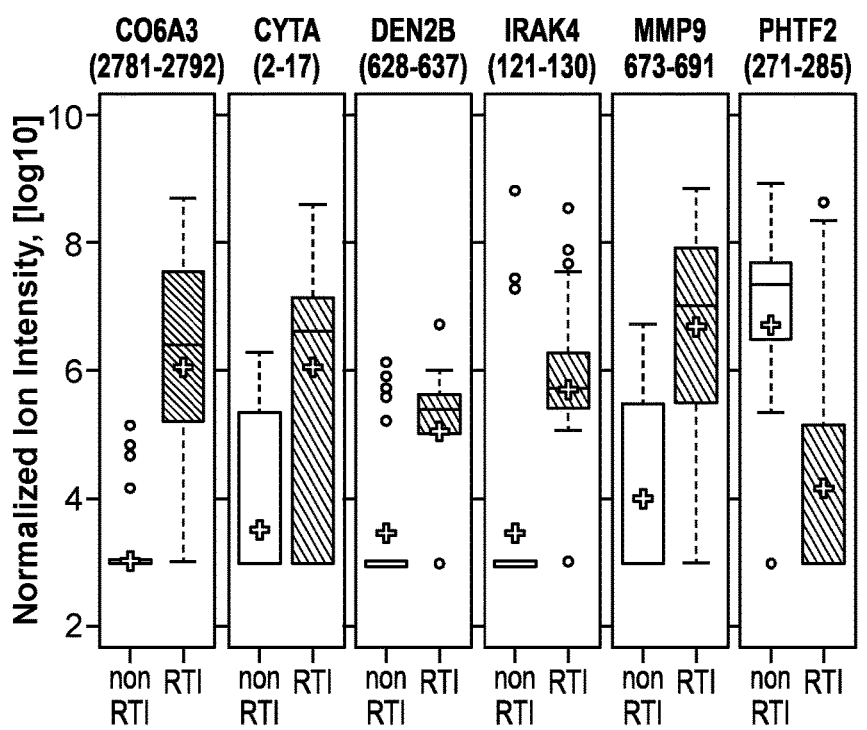
Figure 3D:
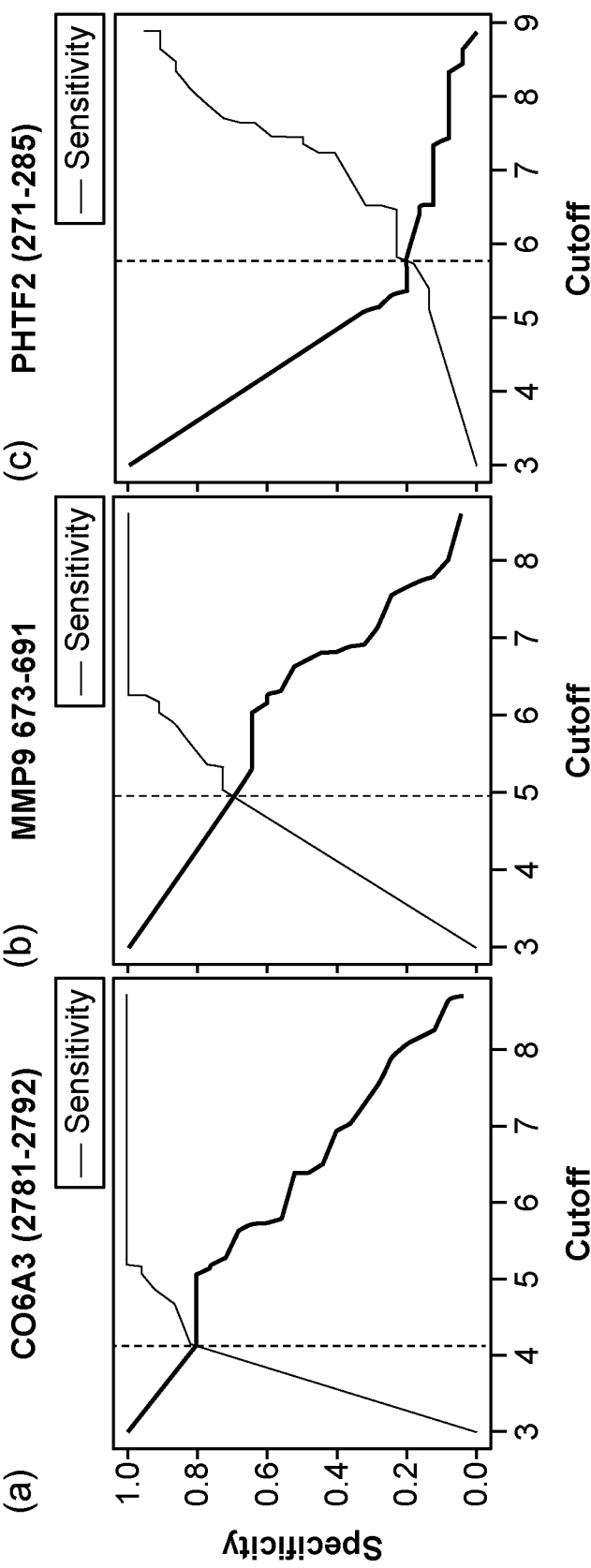

In some implementations, the step of predicting the presence of RTI by calculating a composite score representative of the statistically significant subset of the truncated proteoforms may include using a reference data sample including the statistically significant subset of the truncated proteoforms determining a reference threshold mass spectra intensity value (cut-off value in step 409) for each truncated proteoform as the value equal to the normalized mass spectra intensity value ($\log_{10}$) related to the intersection of the specificity and sensitivity curves in the ROC for each proteoform (see FIG. 3D). Next, an indicative score of 1 may be assigned to a truncated proteoform if the measured intensity value of that truncated proteoform is greater than or equal to the reference threshold intensity value and an indicative score of 0 if the measured intensity value of that proteoform is less than the reference threshold intensity value. In step 407, The indicative scores assigned to each statistically significant truncated proteoform in the subset are summed up (added) to calculate a composite score representative of the statistically significant subset of the truncated proteoforms for each collected sample. A cut-off classifier value representing the minimum number of statistically significant truncated proteoforms in the subset required to predict the presence of RTI may be determined.

In some implementations, the presence of RTI may be predicted if the composite score is greater than or equal to the cut-off classifier value. The cut-off classifier value may be determined by generating a confusion matrix for each classifier value including n, (n–1), (n–2), . . . , 0 where n is the total number of statistically significant proteoforms in the subset using the indicative scores (0 or 1) of each proteoform as predictive indicators and the baseline data as actual indicators (0 or 1) of RTI. A RTI prediction accuracy may be calculated using the confusion matrix for each classifier value defined as the ratio of the sum of true positive and true negative results (TP+TN) to the total number of collected liquid samples. (Table 5). The cut-off classifier value may be determined as the classifier value including the number of truncated proteoforms required to yield a RTI prediction accuracy of at least about 90%.

In some implementations, the step of identifying a class of statistically significant truncated proteoforms using t-test may include applying a two-tailed unpaired t-test to the truncated proteoforms in step 404 and adjusting the p-values by the application of 0.05 false-discovery rate (FDR) using the Benjamini-Hochberg method in step 405. The downselecting step may include selecting truncated proteoforms with a p-value of less than 0.05 resulting from multiple logistic regression analysis to yield the statistically significant subset of the truncated proteoforms.

In some implementations, the example method 400 may further determine whether the composite score is statistically significant for distinguishing between RTI and non-RTI patients if the p-value of the composite score resulting from multiple logistic regression analysis of variables including one or more of age, gender, race, ethnicity, primary diagnosis, medication, sample collection time, microorganism identification information, white blood cell count, body temperature, fraction of inspired oxygen (FiO2) content, pulmonary radiography, individual scores of the truncated proteoforms in the subset, or composite score is less than 0.001.

Figures 5A, 5B, 5C:
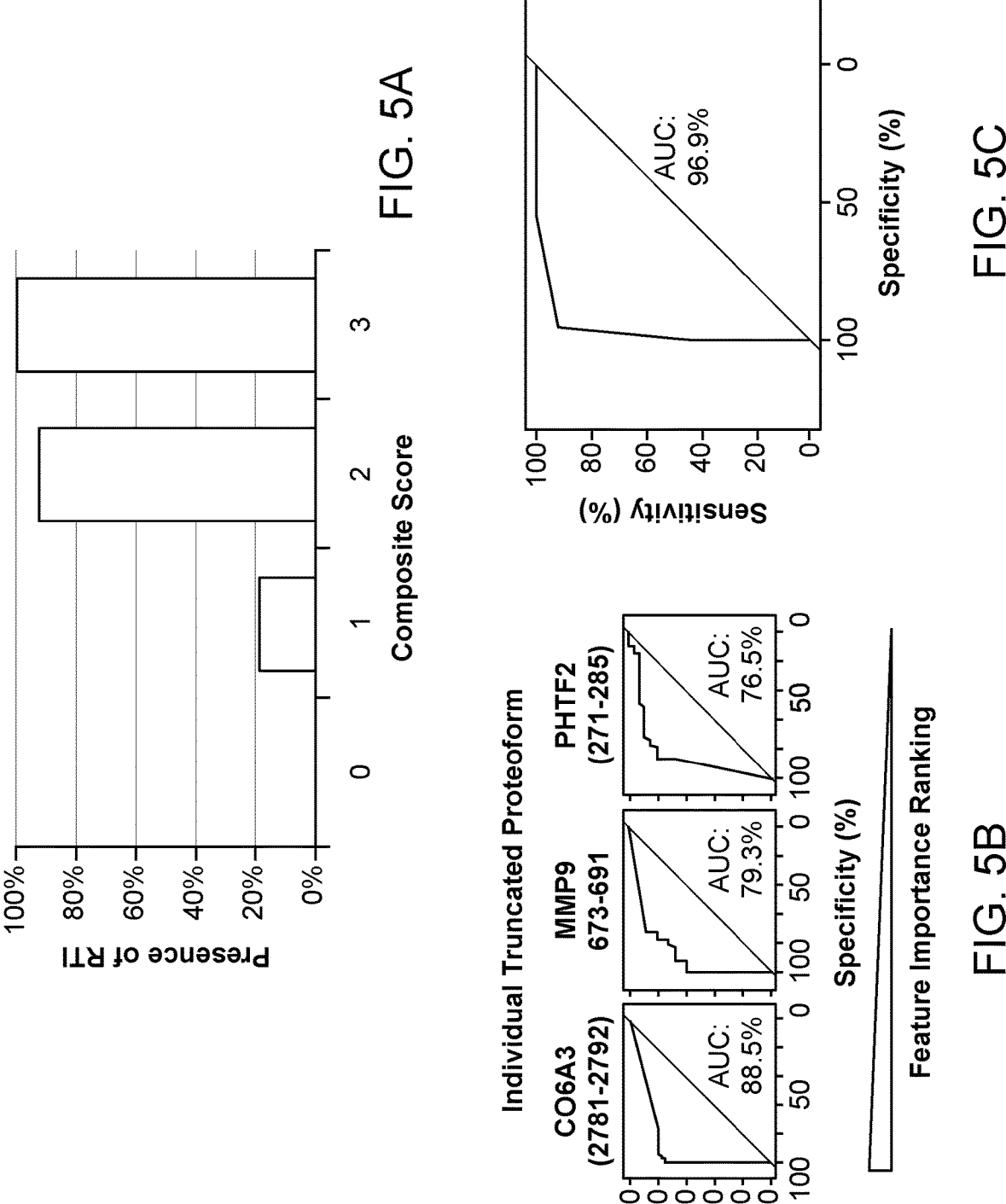

In some implementations, the presence of RTI may also be predicted by calculating the area under the curve (AUC) of the combined receiver operating characteristic (ROC) curve representative of the statistically significant subset of the class of truncated proteoforms in step 410 (FIG. 5A). The ROC representative of all of the proteoforms in the statistically significant subset may be constructed wherein the specificity (TN/TN+FP) and sensitivity (TP/TP+FN) values for the ROC are calculated using the indicative scores of each proteoform as the predictive indicators of RTI and the baseline data as actual indicators of RTI. The area under curve (AUC) may be determined using the ROC representative of all of the proteoforms in the statistically significant subset. An AUC value greater than at least about 95% may be indicative of the presence of RTI. The statistically significant subset of the class of truncated proteoforms may include one or more of CO6A3 (amino acid 2781-2792), CYTA (2-17), DEN2B (628-637), IRAK4 (121-130), MMP9 (673-691), or PHTF2 (271-285).

In some implementations, the predictive model for RTI developed using example method 400 may be used for diagnosis of RTI in patients. An example method for diagnosing a respiratory tract infection (RTI) in intubated patients by capturing truncated proteoforms in exhaled breath aerosols may include selectively capturing truncated proteoforms in the exhaled breath aerosols produced by each patient using a packed bed column removably connected to the exhaled air tubing of the ventilator, extracting the truncated proteoforms into one or more collected liquid samples corresponding to each patient, analyzing the collected samples corresponding to each patient including truncated proteoforms using mass spectrometry to obtain raw mass spectra, calculating a composite score for the statistically significant proteoforms in the samples wherein the statistically significant proteoforms are provided by the reference data as previously described, and diagnosing the presence of RTI if the composite score is greater than or equal to the composite score in the referenced data (FIG. 5A) that predicts RTI with an accuracy of greater than at least 90%.

In some implementations, the composite score for the statistically significant proteoforms in the samples may be calculated by determining a normalized mass spectra intensity value (log 10) for each statistically significant truncated proteoform, assigning an indicative score of 1 to a truncated proteoform if the normalized intensity value of a statistically significant truncated proteoform is greater than or equal to its reference threshold intensity value (FIG. 3D) and an indicative score of 0 if the normalized intensity value of a proteoform is less than its reference threshold intensity value, and adding the indicative scores to calculate a composite score representative of the statistically significant subset of the truncated proteoforms in the samples. The example systems and methods disclosed above may also be used for predicting and diagnosing other diseases by capturing truncated proteoforms and other biomarkers in exhaled breath aerosols.

EXAMPLES

Example 1. Capture and Analysis of Exhaled Air Aerosols of Patients Diagnosed with COVID-19 Using an Example Packed Bed Column Connected to a Ventilator Example system 1300 (FIG. 1A) was evaluated in a hospital intensive care unit (ICU) dedicated for treating patients diagnosed with the COVID-19 disease. The flow rate through the packed bed column including about 25 mg of C18 beads (20 μm nominal diameter) in sample capture element 1301 was set at 500 ml/min. Before installing in system 1300, the capture element was washed with 70% acetonitrile once and then thrice with 0.05% TFA. The capture elements were stored at 4° C. before use to prevent drying out of the C18 beads in the packed bed. Exhaled breath aerosol was then collected for about 4 h from each patient at a flow rate of 500 ml/min. After the collection period, the packed bed columns were removed from the collection system. The columns were washed with about 200 µL to about 400 µL of 70% ACN or 70% IPA. The organic solvent was removed from the packed bed column by lyophilization overnight. The organic solvent may also be removed by placing element 1301 on a heating block at about 70° C. for about 30 minutes. The captured aerosol particles were the extracted or resolved using between about 40 µL and 100 µL of 0.05% TFA. The samples were then analyzed using SDS-PAGE electrophoresis and silver staining, MALDI-TOFMS (whole cell top-down proteomics), and bottom-up proteomics.

About 5 µl of total collected sample was used for SDS-PAGE electrophoresis, which was conducted using a Criterion Tris-HCl Gel system (Bio-Rad Laboratories, Hercules, CA). After SDS-PAGE electrophoresis, the SDS-PAGE gel was prepared with a silver staining kit (Thermo Fisher Scientific) for the visualization of protein bands. Bovine serum albumin was used as an internal positive control. Protein bands were observed in all 3 patient samples. Based on the BSA control sample, the protein content in 3 samples was estimated to be at least 100 ng.

For whole cell MALDI-TOFMS analysis, 0.2 µL of analytes was mixed with 0.2 µL of α-Cyano-4-hydroxycinnamic acid MALDI matrix (CHCA) prepared in 70% ACN. The mixture was deposited onto a MALDI sample cap and mass spectra were collected using an example MALDI-TOF mass spectrometry system disclosed in commonly owned Pat. Appl. No. PCT/US20/48042 titled "SYSTEMS AND METHODS OF RAPID AND AUTONOMOUS DETECTION OF AEROSOL PARTICLES," which is incorporated by reference herein in its entirety. MALDI-TOF spectra were collected from the samples of patient #3 and #4. Mass peaks were observed in both samples. The peak patterns generated from MALDI-TOF MS were examined using pattern recognition algorithms for detection and classification.

For bottom-up proteomics, 5 µl of each sample was used. About 50 µl of 50 mM ammonia bicarbonate (pH 8.5) was added to each sample. Protein reduction was conducted by adding dithiothreitol to a final concentration of 5 mM and incubating for 30 min at 37° C. After reduction, protein alkylation was followed by adding iodoacetamide to a final concentration of 15 mM and incubating for 1 h at room temperature. Trypsin (Thermo Fisher Scientific) was used for an overnight protein digestion. After digestion, peptides were cleaned up using C18-packed tips (Glygen, Columbia, MD). The peptide samples in 20 µl of 0.1% formic acid were then prepared for mass spectrometry analysis, including MALDI-TOF mass spectrometry. Samples were processed using an EASY-nLC 1000 system (Thermo Fisher Scientific) coupled to a LTQ Quadrupole-Orbitrap mass spectrometer (Thermo Fisher Scientific). For tandem mass spectrometry analysis, peptides were loaded into an Acclaim PepMap 100 C18 trap column (0.2 mm×20 mm, Thermo Fisher Scientific) with a flow rate of 5 µl/min and separated on an EASY-Spray HPLC Column (75 µm×150 mm, Thermo Fisher Scientific). HPLC gradient was conducted using 5%-55% of the mobile phase (75% acetonitrile and 0.1% formic acid) with a flow rate of 300 nl/min for 60 min.

Mass spectrometry data collection was conducted in the data dependent acquisition mode. Precursor scanning resolution was set to 30,000 and product ion scanning resolution 15,000. Product ion fragmentation was achieved using high energy collision-induced disassociation with 30% total energy. The bottom-up proteomics raw data files were processed with MaxQuant Andromeda software (maxquant.org) against the "human" and "SARS-COV-2" protein database (uniprot.org) following the standard recommendations and instructions.

Human protein database included 20,395 reviewed proteins and SARS-COV-2 protein database included 13 reviewed proteins. Liquid chromatography profiles and peptide fingerprints generated from the digested peptides were identified using LC-MS and MALDI-TOF MS in all three patient samples. In total, 222 proteins were identified in all three patient samples. Most proteins were found to originate from human blood, indicating active interaction between lungs and blood. As shown in Table 1, typical lung proteins and SARS-COV-2 protein were identified:

TABLE 1

| Proteins identified from exhaled air aerosols collected from patients diagnosed with COVID-19. | |
| --- | --- |
| Protein identification list | Mol. weight [kDa] |
| sp\|P0DTD1\|R1AB_SARS2 Replicase polyprotein lab OS = Severe acute respiratory syndrome coronavirus 2 OX = 2697049 GN = rep PE = 1 SV = 1 | 794.05 |
| sp\|Q9HC84\|MUC5B_HUMAN Mucin-5B OS-Homo sapiens OX = 9606 GN = MUC5B PE = 1 SV = 3 | 596.33 |
| sp\|P02671\|FIBA_HUMAN Fibrinogen alpha chain OS = Homo sapiens OX = 9606 GN = FGA PE = 1 SV = 2 | 94.972 |
| sp\|P02768\|ALBU_HUMAN Serum albumin OS = Homo sapiens OX = 9606 GN = ALB PE = 1 SV = 2; | 69.366 |
| sp\|P02675\|FIBB_HUMAN Fibrinogen beta chain OS = Homo sapiens OX = 9606 GN = FGB PE = 1 SV = 2 | 55.928 |
| sp\|Q8TDL5\|BPIB1_HUMAN BPI fold-containing family B member 1 OS = Homo sapiens OX = 9606 GN = BPIFB1 PE = 1 SV = 1 | 52.441 |
| sp\|P63261\|ACTG_HUMAN Actin, cytoplasmic 2 OS = Homo sapiens OX = 9606 GN = ACTG1 PE = 1 SV = 1;sp\|P60709\|ACTB_HUMAN Actin, cytoplasmic 1 OS = Homo sapiens OX = 9606 GN = ACTB PE = 1 SV = 1 | 41.792 |
| sp\|P35247\|SFTPD_HUMAN Pulmonary surfactant-associated protein D OS = Homo sapiens OX = 9606 GN = SFTPD PE = 1 SV = 3 | 37.728 |
| sp\|P02647\|APOA1_HUMAN Apolipoprotein A-I OS = Homo sapiens OX = 9606 GN = APOA1 PE = 1 SV = 1 | 30.777 |
| sp\|Q8IWL2\|SFTA1_HUMAN Pulmonary surfactant-associated protein A1 OS = Homo sapiens OX = 9606 GN = SFTPA1 PE = 1 SV = 2;sp\|Q8IWL1\|SFPA2_HUMAN Pulmonary | 26.242 |

TABLE 1-continued

Proteins identified from exhaled air aerosols collected from patients diagnosed with COVID-19.

| Protein identification list | Mol. weight [kDa] |
|---|---|
| surfactant-associated protein A2 OS = Homo sapiens OX = 9606 GN = SFTPA2 PE = 1 SV = 1 | |
| sp\|P68871\|HBB_HUMAN Hemoglobin subunit beta OS = Homo sapiens OX = 9606 GN = HBB PE = 1 SV = 2 | 15.998 |
| sp\|P69905\|HBA_HUMAN Hemoglobin subunit alpha OS = Homo sapiens OX = 9606 GN = HBA1 PE = 1 SV = 2 | 15.257 |
| sp\|Q99879\|H2B1M_HUMAN Histone H2B type 1-M OS = Homo sapiens OX = 9606 GN = H2BC14 PE = 1 SV = 3;sp\|Q99877\|H2B1N_HUMAN Histone H2B type 1-N OS = Homo sapiens OX = 9606 GN = H2BC15 PE = 1 SV = 3;sp\|Q93079\|H2B1H_HUMAN Histone H2B type 1-H OS = Homo sapiens OX = 9606 GN = HIST1H2BH PE | 13.989 |
| sp\|P0DJI8\|SAA1_HUMAN Serum amyloid A-1 protein OS = Homo sapiens OX = 9606 GN = SAA1 PE = 1 SV = 1 | 13.532 |
| sp\|P06702\|S10A9_HUMAN Protein S100-A9 OS = Homo sapiens OX = 9606 GN = S100A9 PE = 1 SV = 1 | 13.242 |
| sp\|P02656\|APOC3_HUMAN Apolipoprotein C-III OS = Homo sapiens OX = 9606 GN = APOC3 PE = 1 SV = 1 | 10.852 |
| sp\|P11684\|UTER_HUMAN Uteroglobin OS = Homo sapiens OX = 9606 GN = SCGB1A1 PE = 1 SV = 1 | 9.9937 |

Example 2. Prediction of RTI by Capturing Exhaled Aerosol Samples from Intubated Patients with Respiratory Tract Infection From 30 intubated patients in the neurological ICUs at The Johns Hopkins Hospital, 47 exhaled aerosol samples (liquid) were collected. Clinical parameters such as age, gender, race, ethnicity, primary diagnosis, medication, sample collection time, microorganism identification information, white blood cell test, body temperature, fraction of inspired oxygen ($FiO_2$) test, and pulmonary radiography were also collected. Positive respiratory tract infection was identified based on clinical criteria by the physicians and when the tract samples, including sputum, endotracheal tube sample (ET), or bronchoalveolar lavage (BAL), were cultured positive in the clinical laboratory at The Johns Hopkins Hospital. This clinical trial data represented baseline data for the analysis described below.

For exhaled aerosol collection, example system 1300 was used. The sample capture element included C18 resin beads having a nominal diameter of between about 12 μm and about 20 μm. The resin beads were packed between two porous polymeric frit discs. The internal diameter of the sample capture element was about 7 mm. The length of the packed bed column was about 3 mm. One capture element was used for each aerosol sample. The column was connected to a tee-fitting installed in the exhaust tubing on the mechanical ventilator. The packed bed was washed water before installing in system 1300. The collection column was connected to a $CO_2$ sensor (Gas Sensing Solutions Ltd, United Kingdom) and a mini diaphragm pump (Parker Hannifin Corporation, Cleveland, OH). The flow rate of the pump was set up to 0.5 liter/minute. The $CO_2$ sensor was used to record individual exhaled $CO_2$ level in the exhaust tubing on the mechanical ventilator. After sample collection, the columns were disinfected (decontaminated). The columns were then eluted with about 300 μL of 70% isopropyl alcohol (IPA) to extract proteins and peptides. The solvent was then removed by an overnight lyophilization. After lyophilization, about 20 μL to about 50 μL of 0.05% TFA was added to each sample for LC-MS/MS analysis.

For LC-MS analysis, about 18 μL of each sample was injected into a microflow C18 column (Acclaim™ PepMap™ 100, 75 μm×2 μm×250 mm, Thermo Fisher Scientific) and proteins were separated using a gradient of solvent (80% acetonitrile with 0.1% formic acid) from 5% to 70% in 60 minutes using an EASY-nLC 1000 system (Thermo Fisher Scientific). Ion fragmentation was conducted using collision-induced dissociation (CID, 35% collision energy) in a LTQ Orbitrap mass spectrometer (Thermo Fisher Scientific) at a mass resolution of 60,000. Raw mass spectrometry data files were searched against Human Swiss-Prot protein database containing 20387 reviewed entries, and truncated proteoforms were identified using MaxQuant software (Max-Planck-Institute of Biochemistry).

Figure 4:
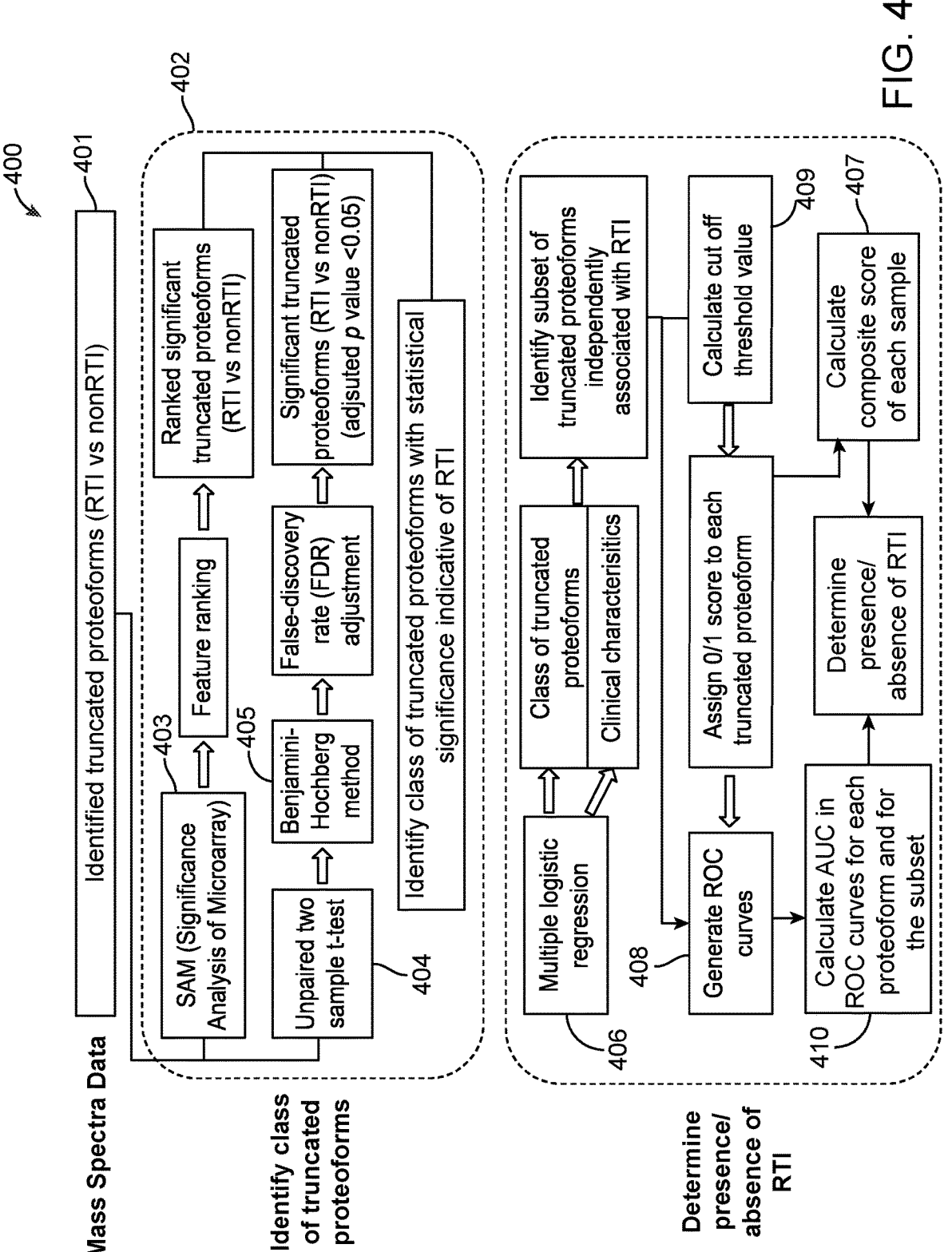

Workflow (FIG. 4) for identifying a class of features (truncated proteoforms) of statistical significance (between non-RTI and RTI samples) included mass spectrometric data processing, feature selection and ranking to identify a class of truncated proteoforms that were statistically significant for predicting RTI, and multiple logistic regression to predict a subset of the class of truncated proteoforms that were statistically significant for predicting RTI. Generally, mass spectrometric features were normalized by total ion chromatography. Data transformation, scaling, and centering was conducted by using the log transformation method. To select the most significant features that contribute to distinguishing between patients without RTI and with RTI, a ranking algorithm for omics, Significance Analysis of Microarrays (SAM), was used. SAM provides feature ranking based on each feature's statistics and fold-change (FIGS. 3B and 4). A two-tailed unpaired t-test was also applied to RTI and non-RTI patients and all the truncated proteoforms identified in this study to acquire raw p values, which were then adjusted by the application of 0.05 false-discovery rate (FDR) using the Benjamini-Hochberg method.

Multiple logistic regression analysis 406 was used to evaluate the correlation between the RTI status of patients

| and variables including measured clinical parameters, and the class of truncated proteoforms having statistical significance identified in step 402. Receiver operating characteristic curves (ROC) were constructed and area under the curve (AUC) were calculated for a subset of statistically significant features (truncated proteoforms) between the RTI and non-RTI groups after p-value adjustment. As previously described, cut-off values for the subset of statistically significant truncated proteoforms were generated based on the specificity and sensitivity values of their respective ROC curves. (FIG. 3D)

263 truncated proteoforms of 80 proteins were identified (Table 2). The identified proteins showed good overlap with the proteins in human breath aerosols and BAL proteomes including blood proteins, lung structure proteins, and cytokines, including blood hemoglobin subunits, S100-A9, S100-A12, albumin, zinc-alpha-2-glycoprotein, and zinc finger homeobox protein 4, uteroglobin, alpha-actinin-1, desmoglenin-1, filamin-A, mucin-5B, and mucin-19, interleukin-1 receptor-associated kinase 4 and matrix metalloproteinase-9. The distribution of truncated proteoforms in each sample showed a greater number of truncated proteoforms in samples of intubated patients with RTI. Further, this difference in the number of truncated proteoforms identified in the exhaled aerosol samples of RTI patients and non-RTI patients was statistically significant (FIG. 3A). In the Box and Whisker plot (FIG. 3A), the boxes indicate quartiles, and the horizontal lines within each box are indicative of the median count in each case. The whiskers related to each "box" indicate the maximum and minimum of each range. The mean count in each case is indicated with a cross mark. In samples collected from intubated patients with RTI, about 125 truncated proteoforms were identified; the number of truncated proteoforms in intubated patients without RTI was about 55 (FIG. 3A).

truncated proteoforms, and proteoform CO6A3 was found to be the significant feature (truncated proteoform) in the list (FIG. 3B). The distribution of the six truncated proteoforms is shown in FIG. 3C and Table 3.

As shown in FIG. 3C, the mass spectra ion intensity of each truncated proteoform in samples of RTI patients was significantly higher than that of non-RTI patients, with the exception of the proteoform corresponding to protein PHTF2. After FDR adjustment at p=0.05, all 6 truncated proteoforms showed statistical significance between the two groups (Table 3). These six proteoforms are characteristic of respiratory tract infections (such as pneumonia, empyema) caused by a variety of bacteria and fungi, including *Pseudomonas aeruginosa, Klebsiella pneumoniae, Citrobacter koseri*, and methicillin resistant (MRSA) *Staphylococcus aureus*, ESKAPE, *Enterococcus faecium, Acinetobacter baumannii*, and *Enterobacter* spp.

In FIG. 3D, the x-axis intensity values (arbitrary units generated in the mass spectrometer) of each identified proteoform were extracted from MaxQuant searching results. Each sample was first normalized by using total intensity values. Missing values (zero values) were replaced by 1000, which is two magnitudes lower than the lowest intensity value observed in the samples. Subsequently, the values were transformed with the logarithm with base 10. For example, a value of 10000 will be 5 after data transformation. To evaluate using the six truncated proteoforms for RTI determination, multiple logistic regression was conducted using variables that included the clinical parameters (age, gender, WBC count, body temperature, inspired oxygen content) of the patients and the identified proteoforms. A multiple logistic regression model was constructed to include the truncated proteoforms as predictors by using glm( ) function in RStudio.

RStudio is an integrated development environment for the programming language R for statistical computing and

TABLE 2

Protein list related to truncated proteoforms from analysis
of the samples collected from intubated patients.
Swiss-Prot Protein ID

| A4D0S4 | O95744 | P11021 | P35908 | P68870 | Q643R3 | Q96F81 | Q9NWZ3 |
| A4FU69 | P00441 | P11684 | P40121 | P68871 | Q7Z5P9 | Q96M83 | Q9NXW2 |
| A5PLN9 | P01040 | P12111 | P47874 | P69905 | Q86UP3 | Q96ME1 | Q9NZ32 |
| A8MX34 | P01834 | P12814 | P49619 | P78524 | Q8IV20 | Q96QF7 | Q9NZJ4 |
| O14523 | P01876 | P13645 | P50748 | Q02413 | Q8N394 | Q99985 | Q9UHL4 |
| O14640 | P02749 | P14780 | P54198 | Q02447 | Q8N3S3 | Q9C005 | Q9UKT7 |
| O14950 | P02768 | P21333 | P59665 | Q13535 | Q8NBR0 | Q9C0A1 | Q9ULT0 |
| O75494 | P04083 | P22894 | P60660-2 | Q14692 | Q8TDL5 | Q9C0D6 | Q9Y2F5 |
| O75594 | P04264 | P24158 | P61626 | Q2M2D7 | Q92608 | Q9H799 | Q9Y5X3 |
| O95069 | P06702 | P35527 | P63261 | Q53RT3 | Q93038 | Q9H8H0 | Q9Y6S9 |

For identification of a class of statistically significant truncated proteoforms contributing to the separation between RTI and non-RTI samples, SAM analysis and the Benjamini-Hochberg method were used. Both methods provide statistical significance analysis with the False Discovery Rate (FDR) adjustment (at p=0.05) was used for feature reduction. SAM analysis provides feature importance ranking based on the separation power between RTI and non-RTI samples. Six truncated proteoforms, CO6A3 (amino acid 2781-2792), MMP9 (673-691), PHTF2 (271-285), IRAK (121-130), CYTA (2-17), and DEN2B (628-637), were found to be statistically significantly different between the two groups. (FIG. 3B). SAM analysis ranked all the six graphics. GLM in R supports non-normal distributions and can be implemented in R through glm( ) function that takes various parameters and allows the user to apply various regression models. Three truncated proteoforms CO6A3, MMP9 and PHTF2 were downselected as a statistically significant subset of the class of proteoforms. These three proteoforms significantly correlated with the presence of RTI (Model 1, Table 4). The most significant truncated proteoform was found to be MMP9 with a p value of 0.006 (Table 4). In Table 4, "variable" means the factors that were included in the multiple logistic regression analysis. The variables in Model 1 include the clinical parameters of patients and the six truncated proteoforms.

TABLE 3

Listing of six statistically significant truncated proteoforms for
distinguishing between RTI and non-RTI patients.

| | | | | SAM Analysis | | Benjamini-Hochberg Method | |
| | | | | | | p Values | |
| | Truncated Proteoforms | | | Fold Change | | | |
| Protein | Amino Acid | Sequence | Score(d) | (RTI/nonRTI) | Raw | Adjusted* |
|---|---|---|---|---|---|---|
| CO6A3 | 2781-2792 | KEVYTFASEPND | 3.03 | 1.83 | 7.4E-08 | 2.0E-05 |
| MMP9 | 673-691 | RCQDRFYWRVSSRSELNQV | 2.79 | 1.67 | 8.3E-07 | 1.1E-04 |
| PHTF2 | 271-285 | TETDNGYVSLDGKKT | 2.61 | -1.76 | 1.0E-06 | 9.1E-04 |
| IRAK4 | 121-130 | QQKQMPFCDK | 2.26 | 1.58 | 2.6E-05 | 1.7E-03 |
| CYTA | 2-17 | IPGGLSEAKPATPEIQ | 2.01 | 1.53 | 3.8E-04 | 0.02 |
| DEN2B | 828-637 | RGKKRLKKLS | 1.86 | 1.51 | 3.1E-04 | 0.02 |

TABLE 4

Multiple logistic regression analysis of variables used for distinguishing
between patients with RTI and non-RTI patients.

| | Variable | Coefficient | Standard Error | t stat | p-value |
|---|---|---|---|---|---|
| Model 1 | Age | 2.E-04 | 0.003 | 0.089 | 0.930 |
| | Gender | 0.143 | 0.103 | 1.393 | 0.172 |
| | white blood cells (WBCS) | 0.003 | 0.012 | 0.227 | 0.822 |
| | body temperature | -0.014 | 0.013 | -1.096 | 0.280 |
| | fiO$_2$ % | 0.002 | 0.004 | 0.437 | 0.665 |
| | CO6A3 (2781-2782) | 0.082 | 0.039 | 2.108 | 0.042* |
| | MMP9 (673-691) | 0.079 | 0.027 | 2.934 | 0.006** |
| | PHTF2 (271-285) | -0.055 | 0.025 | -2.199 | 0.034* |
| | IRAK4 (121-130) | 0.051 | 0.032 | 1.589 | 0.121 |
| | CYTA (2-17) | 0.030 | 0.034 | 0.891 | 0.379 |
| | DEN2B (628-637) | -0.046 | 0.051 | -0.890 | 0.380 |
| Model 2 | Age | -3.E-04 | 0.003 | -0.114 | 0.910 |
| | Gender | 0.158 | 0.098 | 1.608 | 0.116 |
| | white blood cells (WBCs) | 0.004 | 0.011 | 0.330 | 0.743 |
| | body temperature | -0.006 | 0.009 | -0.632 | 0.531 |
| | fiO$_2$ % | -0.002 | 0.004 | -0.460 | 0.648 |
| | Composite Score (score = 3) | 0.361 | 0.101 | 3.586 | 9.E-04*** |
| | Score 1 (CO6A3, score = 1) | 0.E+00 | 0.E+00 | N/A | N/A |
| | Score 2 (MMP9, Score = 1) | -0.020 | 0.176 | -0.113 | 0.911 |
| | Score 3 (PHTF2, score = 1) | 0.035 | 0.145 | 0.242 | 0.810 |

*p value < 0.05,
**p value < 0.01,
***p value < 0.001.

The accuracy of predicting RTI using one or more proteoforms in the statistically significant subset of the class of proteoforms was next examined. The clinical trials baseline data including 47 exhaled breath aerosol samples was used as actual indicators of the RTI. The presence or absence of RTI was predicted for each classifier value including n, (n–1), (n–2), . . . , 0 where n is the total number of statistically significant proteoforms in the subset. In this example, n=3. A confusion matrix (Table 5) was then generated for each classifier value 0, 1, 2, 3. The confusion matrix for n=2 resulted in accuracy of 93.6% (TN+TP/47) with precision of 95.8% (TP/TP+FP). The prediction accuracy was 53.2%, 78.7%, 93.6%, and 70.2% for n=0, 1, 2, 3, respectively. The prediction precision was 53.2%, 71.4%, 95.8% and 100% for n=0, 1, 2, 3 respectively. The cut-off classifier value was taken as n=2 as the prediction accuracy was greater than 90%. A composite score in step 407 was then calculated using mass spectrometry analysis of a reference sample. First, using a reference sample including each of the statistically significant subset of the truncated proteoforms CO6A3, MMP9 and PHTF2, a reference threshold mass spectra intensity value was determined as the value equal to the normalized mass spectra intensity value (log$_{10}$) related to the intersection of the specificity and sensitivity curves in the ROC for each proteoform. (FIG. 3D).

Next, using the collected liquid samples, a measured mass spectra intensity value for each statistically significant truncated proteoform in the subset was determined. For each liquid sample analyzed, a score of 1 was assigned to a truncated proteoform in the subset if the measured intensity value of that truncated proteoform was greater than or equal to its reference threshold intensity value. A score of 0 was assigned if the measured intensity value of a proteoform in the collected liquid sample was less than the reference threshold intensity value. For each liquid sample, the individual scores assigned to each truncated proteoform in the subset was added to calculate the composite score representative of the statistically significant subset of the truncated proteoforms in the collected liquid sample. In this example, the composite score could have a minimum value of 0 and maximum value of 3.

TABLE 5

Confusion Matrix for Predicting RTI in the 47 exhaled breath aerosol samples collected during clinical trial using n = 2.

|  |  | Predicted | |
| --- | --- | --- | --- |
|  |  | 0 | 1 |
| Actual | 0 | 21 (TN) | 1 (FP) |
|  | 1 | 2 (FN) | 23 (TP) |
|  | Total | 23 | 24 |

TN = True Negative,
TP = True Positive,
FN = False Negative,
FP = False Positive.

RTI may be predicted by determining whether the composite score calculated as described above is greater than or equal to the cut-off classifier value as previously described. A composite score of 3 would be a strong indicator of the presence of RTI in this example. The probability of RTI prediction based on the composite score using the 47 liquid collected samples showed that a score of 1 was associated with a probability of predicting RTI of 18%, a score of 2 with a probability of 92%, and a score of 3 with a probability of 100% (FIG. 5A). Out of 47 samples, 12 samples had a score of 0, and all 12 samples were non-RTI samples, which gives 0% probability for predicting RTI. 11 of 47 samples had a score of 1, and 2 of 11 samples were RTI positive, which gave 18% probability of predicting RTI. 13 of 47 samples had a score of 2, and 12 of 13 samples were RTI positive, which gave 92% probability of predicting RTI. 11 of 47 samples had score of 3, and all 11 samples were RTI positive, which gave 100% probability in predicting RTI.

In Table 4, Score1, Score 2, and Score3 represent the scores calculated from individual truncated proteoforms CO6A3, MMP9, and PHTF2, respectively, which was equal to 1 in each case. Table 4 shows that the individual scores were not statistically significant in distinguishing between RTI and non-RTI patients when examined using multiple logistic regression analysis (Model 2). However, the composite score was found to be statistically significant with a p-value less than 0.001. The ability of using the three statistically significant proteoforms CO6A3, MMP9, PHTF2 to distinguish between RTI and non-RTI patients was also examined using AUC (area under the ROC curve) values in step 410. The AUC values (FIG. 5B) suggest that each individual truncated proteoform may not be useful in distinguishing between RTI and non-RTI patients; that is, they may not be useful in class separation between RTI and non-RTI patients as the AUC value for CO6A3, MMP9 and PHTF2 truncated proteoforms was 88.5%, 79.3% and 76.5%, respectively. A linear regression model was constructed using multiple logistic regression with all three truncated proteoforms, and the AUC was found to be 96.9% (FIG. 5C). This high AUC value suggests that these three truncated proteoforms, when taken together, may be used as the basis for distinguishing between patients with RTI and those without RTI and confirms or complements the prediction using the calculation of a composite score. An excellent model has AUC of about 1 which indicates good separability between RTI and non-RTI patients.

Example 3. Tuberculosis Prediction by Capturing Exhaled Aerosol Samples from Patients with Respiratory Tract Infection From a cohort of intubated patients in the neurological ICUs at The Johns Hopkins Hospital, exhaled aerosol samples (liquid) were collected. Clinical parameters such as age, gender, race, human immunodeficiency virus ("HIV") status, ethnicity, primary diagnosis, medication, sample collection time, microorganism identification information, white blood cell test, body temperature, fraction of inspired oxygen ($FiO_2$) test, and pulmonary radiography were also collected. Positive respiratory tract infection was identified based on clinical criteria by the physicians and when the tract samples, including sputum, endotracheal tube sample (ET), or bronchoalveolar lavage (BAL), were cultured positive in the clinical laboratory at The Johns Hopkins Hospital. Additionally, clinical trial data and the clinical parameters disclosed above was collected from a clinic in South Africa from another cohort of non-intubated patients who were tested for tuberculosis ("TB"). These clinical trial data from a total of 31 patients represented baseline data for the analysis described below.

Exhaled air was captured from the two cohorts of patients to examine if proteoform biomarkers aerosolized in exhaled air and captured from these patients may be used to predict tuberculosis infection. For exhaled aerosol collection from the intubated patients, example system 1300 (referring to FIGS. 1A-1B) was used. The sample capture element 1301 included C18 resin beads having a nominal diameter of between about 12 μm and about 20 μm. The resin beads were packed between two porous polymeric frit discs. The internal diameter of the sample capture element was about 7 mm. The length of the packed bed column was about 3 mm. One capture element was used for each aerosol sample. The column was connected to a tee-fitting installed in the exhaust tubing on the mechanical ventilator. The packed bed was washed water before installing in system 1300. The collection column was connected to a $CO_2$ sensor (Gas Sensing Solutions Ltd, United Kingdom) 1311 and a mini diaphragm pump 1308 (Parker Hannifin Corporation, Cleveland, OH). The flow rate of the pump was set up to 0.5 liter/minute. The $CO_2$ sensor 1311 was used to record individual exhaled $CO_2$ level in the exhaust tubing on the mechanical ventilator. After sample collection, the columns were disinfected (decontaminated). The columns were then eluted with about 300 μL of 70% isopropyl alcohol (IPA) to extract proteins and peptides captured from exhaled air. The solvent was then removed by an overnight lyophilization.

Figure 6:
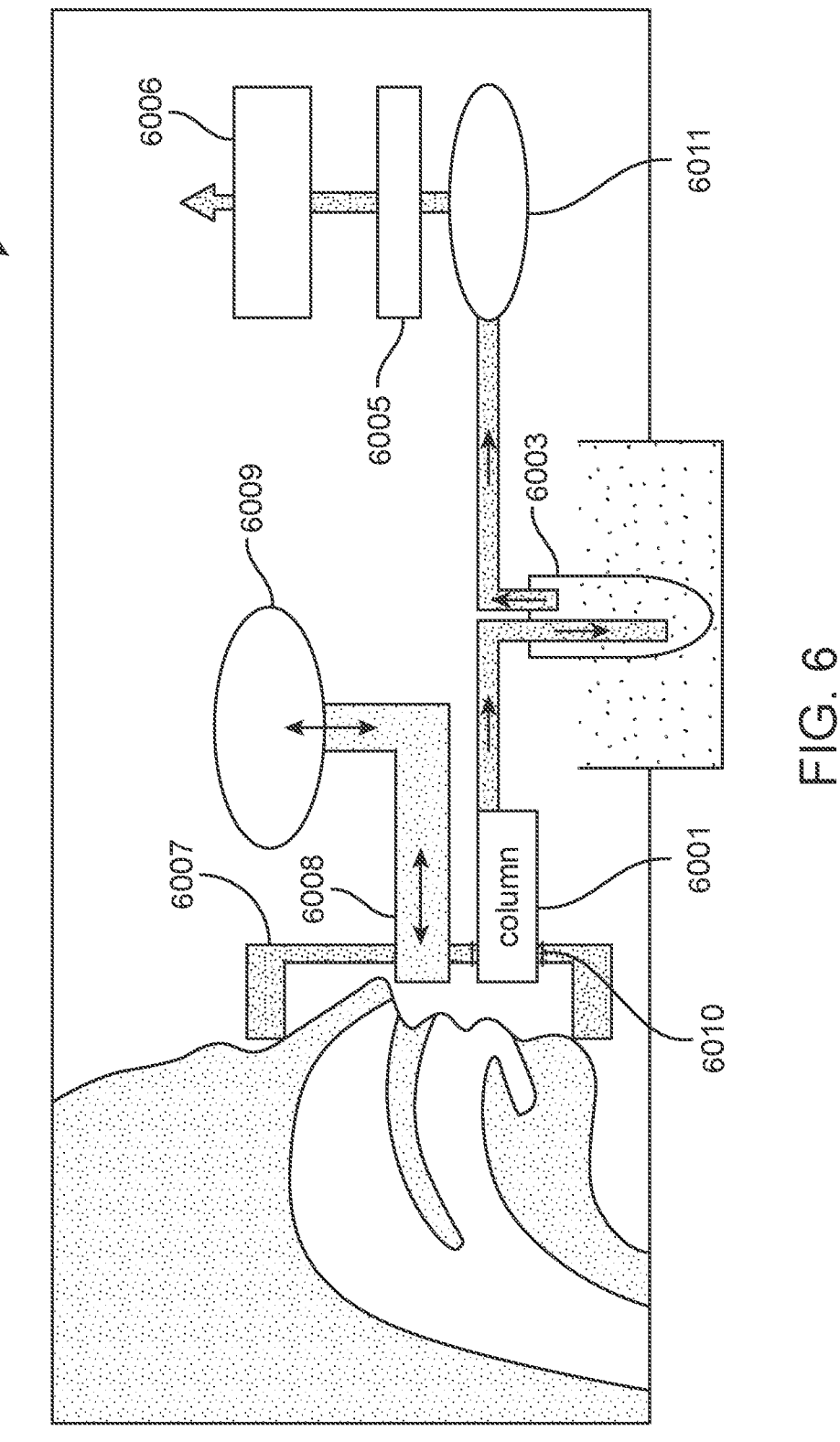
FIG. 6 shows a schematic diagram of another example exhaled breath aerosol particle capture system including a packed bed column, according to some implementations.

For exhaled air (also referred to as exhaled breath) capture from non-intubated patients, the sample capture element was removably inserted into a mask as disclosed below. FIG. 6 shows a schematic diagram of an example exhaled air aerosol non-volatile particle capture system 6000 including a packed bed column, according to some implementations. In some implementations, the example exhaled breath capture element 6001 may include a packed bed column including C18-bonded resin beads (not shown for simplicity). These resin beads may have C18 functional groups immobilized on the surface. In some implementations, sample capture element 6001 may be connected or removably installed to a first aid CPR rescue mask 6007 with minor modifications.

In some implementations, the stem 6008 of mask 6007 that usually connects to a resuscitation bag may be modified to removably connect to a HEPA filter 6009. The HEPA filter prevents contamination of inhaled breath by contaminants from ambient air. The oxygen inlet 6010 to the mask may be located below the stem and may be configured to be proximate to the chin of a human subject when mask 6007 is worn by the subject. In some implementations, sample capture element 6001 may be removably inserted into mask 6007 through inlet 6010 or otherwise removably connected to or inserted into mask 6007 to form a substantially leak-tight fit with mask 6007. Mask 6007 may include elastic bands or ties that may be looped behind the head of a human subject to seal the mask to the face of the patient. Mask 6007, as described above, prevents direct contact between the mouth and the inlet of the column in element 6001, minimizes or eliminates contamination of the column inlet by saliva, and also maximizes non-volatile organic particle collection from exhaled breath.

In some implementations, trap 6003 may be immersed in ice water and may be installed downstream of sample capture element 6001. The flow rate (air draw rate) using pump 6006 may be controlled using needle valve 6005 to pull exhaled air at a flow rate of about 600 mL/min. In some implementations, a nominal flow rate of between about 200 ml/min and 600 ml/min may be used. An optional HEPA filter 6011 may be installed between trap 6003 and needle valve 6005. Other fluidic components such as a check valve may be installed in exhaled breath aerosol non-volatile particle capture system 6000 to prevent backflow into the packed bed column disposed in sample capture element 6001. $CO_2$ in exhaled breath passes through the column bed in element 201. To determine if exhaled breath sample volume and/or breathing maneuvers are adequate, a $CO_2$ sensor (not shown for simplicity) may be disposed between the outlet of breath capture element 6001 and trap 6003. $CO_2$ monitoring allows for an approximation of exhaled air volume. The capture element 6001 may be disposed to be in fluid communication with a subsystem 1313 (referring to FIG. 1B) through port 1314, which may include a quick connect/disconnect coupling. The pump 6006 and other sensors and fluidic components may be disposed in subsystem 1313.

In some implementations, a particle counter (not shown for simplicity) may also be installed between the outlet of element 6001 and trap 6003 to detect the size and number for particles exiting the packed bed column, which may also be used to detect saturation of the bed and breakthrough of nonvolatile organic molecules from the packed bed column. Example exhaled breath aerosol non-volatile particle capture system 6000 may also include a sample capture element 6001 bypass line (not shown for simplicity) to enable standardization of breath volume prior to routing into the column bed in element 6001. A $CO_2$ sensor and particle counter may also be fluidly connected to the bypass line.

The capacity of solid beads immobilized with functional groups in the packed bed column in capture element 6001 may be between about 0.05 mg (non-volatile organics)/mg beads and about 0.5 mg/mg. The capacity of C18-bonded resin beads in the packed bed column disposed in example sample capture element 6001 may be about 0.1 mg/mg. That is, a column bed having 25 mg C18 beads may have the capacity to trap or adsorb about 2.5 mg of non-volatile organic molecules. Other details related to system 6000 and capture element 6001 are disclosed in commonly owned International Application No. PCT/US22/22964 and PCT/US20/048035, which are incorporated by reference herein in each of their entireties. As previously described, after sample collection, the packed bed columns in capture elements 6001 were disinfected (decontaminated). The columns were then eluted with about 300 µL of 70% isopropyl alcohol (IPA) to extract proteins and peptides captured from exhaled air. The solvent was then removed by an overnight lyophilization.

The extracted samples associated with the captured exhaled breath of both patient cohorts were then analyzed using MALDI-TOFMS (whole cell top-down proteomics). Additional details were previously disclosed in Example 1. Using feature selection algorithms, including significance analysis of microarray ("SAM") and multiple logistic regression analysis, significant features in associated MALDI-TOFMS mass spectra were identified and correlated with disease (TB) status. The example workflow 400 shown in FIG. 4 and described in Example 2 provides additional details related to feature selection of statistical significance to discriminate between TB and non-TB patients in both cohorts.

Proteins identified in the breath samples from the two distinct cohorts included hemoglobin subunits, S100-A9, S100-A12, albumin, mucin-5B, mucin-19, interleukin-2 receptor subunit alpha, and members of the collagen protein family. For identifying a class of statistically significant truncated proteoforms contributing to the separation between TB and non-TB samples, SAM analysis and the Benjamini-Hochberg method were used. Both methods provide statistical significance analysis with the False Discovery Rate ("FDR") adjustment (at $p=0.05$) for feature reduction. Five proteolytic products of infection ("PPI") markers or truncated proteoforms were found to be statistically significant between the two TB and non-TB groups. The five PPI markers (also referred to as truncated proteoforms herein) included interleukin-10 receptor subunit alpha (IL10RA), protein phosphatase 1 regulatory subunit 17 (PPR17), collagen alpha-1(II) chain (COL2A1), collagen alpha-1(JJJ) chain (COL3A1) and complement component C6 (C6). As shown in Table 6, after FDR adjustment at $p=0.05$, all five PPI showed statistical significance between the TB and non-TB groups. These five proteoforms may be considered to be a statistically significant subset of the class of proteoforms for TB detection. To further evaluate using the five truncated proteoforms for discriminating between TB and non-TB patients, multiple logistic regression was conducted using variables that included the clinical parameters (age, gender, WBC count, body temperature, inspired oxygen content) of the patients and the identified proteoforms. A multiple logistic regression model was constructed to include the truncated proteoforms as predictors by using glm( ) function in RStudio.

TABLE 6

| | | | | | SAM Analysis, Fold Change, [Log2] | |
|---|---|---|---|---|---|---|
| Feature Ranking | Sequence | Amino Acids | Name | UniProtKB ID | TB/nonTB | FDR, 0.05 |
| 1 | RDGVPGGPGMRG | 526-537 | COL3A1 | P02461 | 12.5 | 3.16E-70 |
| 2 | GDAGAPGPQGPS | 789-800 | COL2A1 | P02458-1 | 7.9 | 5.01E-11 |
| 3 | KPRRKDTPALHIPPFIPGVF | 62-81 | PPR17 | O96001 | 2.1 | 1.58E-03 |
| 4 | EEMKEVDLPEI | 628-638 | C6 | P13671 | 0.43 | 5.01E-04 |
| 5 | RSNKGMWSKEE | 212-222 | IL10RA | Q13651 | 0.22 | 7.94E-03 |

Listing of five statistically significant PPI biomarkers for distinguishing between TB and non-TB patients.

As shown in Table 7, all five truncated proteoforms or PPJ biomarkers significantly correlated with the presence of TB.

TABLE 7

Multiple logistic regression analysis of variables used for distinguishing between patients with RTI and non-RTI patients.

| | Variable | Coefficient | Standard Error | t stat | p values |
|---|---|---|---|---|---|
| Model 1 | Age | 0.052 | 0.102 | 0.028 | 0.086 |
| | Gender | 0.002 | 0.019 | 1.252 | 0.855 |
| | HIV Status | −0.235 | 0.011 | −0.521 | 0.103 |
| | COL3A1 (526-537) | 0.852 | 0.012 | 3.589 | 0.003** |
| | COL2A1 (789-800) | 0.362 | 0.014 | 4.958 | 0.007** |
| | PPR17 (62-81) | 0.289 | 0.032 | 1.23 | 0.023* |
| | C6 (628-638) | 0.002 | 0.022 | 2.575 | 0.025* |
| | IL10RA (212-222) | 0.014 | 0.036 | 1.477 | 0.031* |
| Model 2 | Age | 0.156 | 0.003 | 0.025 | 0.075 |
| | Gender | 0.003 | 0.025 | 1.284 | 0.635 |
| | HIV Status | −0.338 | 0.126 | 0.325 | 0.079 |
| | Composite Score (score = 6) | 0.896 | 0.233 | 5.899 | 4.7E-4*** |

*p value < 0.05,

**p value < 0.01,

***p value < 0.001.

The most significant truncated proteoform was found to be COL3A1 with ap value of 0.003 (Table 7). In Table 7, "variable" means the factors that were included in the multiple logistic regression analysis. The variables in Model 1 include the clinical parameters of patients and the five truncated proteoforms.

Next, the accuracy of predicting TB using the statistically significant subset of the class of proteoforms was examined. The clinical trials baseline data including 31 exhaled breath aerosol samples was used as actual indicators of the TB. A confusion matrix was then generated as shown in Table 8 below including the combination of five proteoforms listed in Table 7. The composite score shown in Table 7 is the combination of 5 proteoforms, assigning 1 score from each proteoform.

TABLE 8

Confusion Matrix for Predicting TB in the 31 exhaled breath aerosol samples collected during clinical trial.

| | | Predicted | |
|---|---|---|---|
| | | 0 | 1 |
| Actual | Negative (0) | 17 (TN) | 1 (FP) |
| | Positive (1) | 1 (FN) | 12 (TP) |
| | Total | 18 | 13 |

TN = True Negative,
TP = True Positive,
FN = False Negative,
FP = False Positive.

Based on these results, the prediction accuracy (TP+TN/31) for TB was calculated to be 93.5%. Precision (TP/TP+FP) was calculated to be 92.3% and the recall (TP/TP+FN) was found to be 92.3%.

Figure 7:
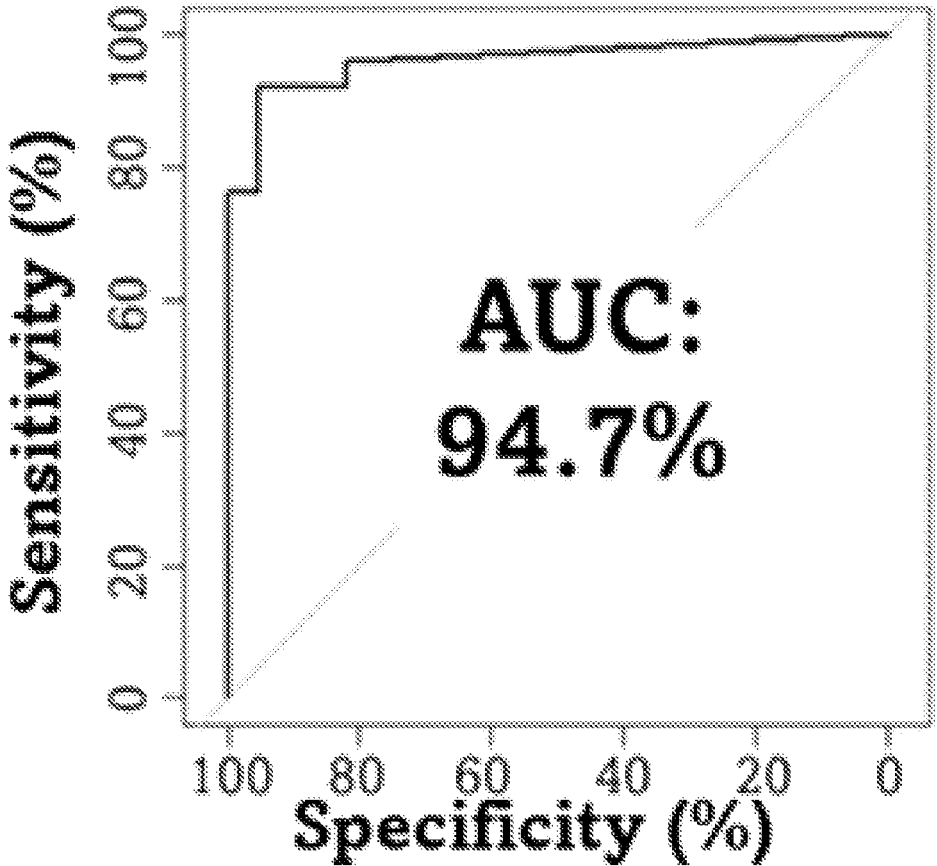
FIG. 7 shows a ROC curve with AUC value generated using statistically significant proteoforms captured from exhaled air for tuberculosis ("TB") detection, according to some implementations.

As shown in Table 7, the composite score was found to be statistically significant with a p-value less than 0.001. A receiver operating characteristic ("ROC") curve was constructed using multiple logistic regression including all five truncated proteoforms. As shown in FIG. 7, the area under the curve ("AUC") was found to be 94.7%, which suggests that these five truncated proteoforms, when taken together, may be used as the basis for discriminating between patients with TB and those without TB and confirms or complements the prediction using the calculation of a composite score. As such, PPI markers (also referred to as truncated proteoforms) may be used to diagnose TB infections.

Accordingly, PPI markers in exhaled breath may be captured and used to noninvasively and accurately detect and diagnose LRTIs. Derived from protease imbalances inherent to TB, these markers demonstrate a potential for TB detection and to improve the timing of initial antibiotic treatment. In addition, once antibiotic treatment is initiated, the disclosed analytical methods may be used to monitor the effect of treatment protocols and may be used to examine discontinuation or modification of antibiotic therapy.

The disclosed example methods and systems may also be used to capture truncated proteoforms in exhaled breath collected using masks worn by patients in an out-patient setting and from ambient air for active case finding or other diagnostic purposes as disclosed in commonly owned International Appl. No. PCT/US22/22964, which is incorporated by reference herein in its entirety.

Although the present disclosure is described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms, even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" or "including" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. N. Ahmed, R. Babaei-Jadidi, S. K. Howell, P. J. Beisswenger & P. J. Thornalley, "Degradation products of proteins damaged by glycation, oxidation and nitration in clinical type 1 diabetes," *Diabetologia* 48, 1590-1603 (2005).
2. Dapeng Chen, Lucia Geis-Asteggiante, Fabio P. Gomes, Suzanne Ostrand-Rosenberg, and Catherine Fenselau, "Top-Down Proteomic Characterization of Truncated Proteoforms," *J. Proteome Res.* 2019, 18, 11, 4013-4019.
3. Hunt, J., "Exhaled breath condensate: An evolving tool for noninvasive evaluation of lung disease," *J. Allergy Clin. Immunol.* 2002; 110:28-34.
4. Allan Lipton, Kim Leitzel, Suhail M. Ali, Hyma V. Polimera, Vinod Nagabhairu, Eric Marks, Angelique E. Richardson, Laura Krecko, Ayesha Ali, Wolfgang Koestler, Francisco J. Esteva, Diana J. Leeming, Morten A. Karsdal, Nicholas Willumsen, "High turnover of extracellular matrix reflected by specific protein fragments measured in serum is associated with poor outcomes in two metastatic breast cancer cohorts," *Intl. J. Cancer,* 2018, 43 (11), 3027-3034.
5. J. Brennan McNeil, Ciara M. Shaver, V. Eric Kerchberger, Derek W. Russell, Brandon S. Grove, Melissa A. Warren, Nancy E. Wickersham, Lorraine B. Ware, W. Hayes McDonald, and Julie A. Bastarache, "Novel Method for Noninvasive Sampling of the Distal Airspace in Acute Respiratory Distress Syndrome," *American J. Respiratory and Critical Care Medicine* 197(8), Apr. 15, 2018.
6. Piero Parchi, Shu G. Chen, Paul Brown, Wenquan Zou, Sabina Capellari, Herbert Budka, Johannes Hainfellner, Patricio F. Reyes, Gregory T. Golden, Jean J. Hauw, D. Carleton Gajdusek, and Pierluigi Gambetti, "Different patterns of truncated prion protein fragments correlate with distinct phenotypes in P102L Gerstmann-Sträussler-Scheinker disease," *Neuroscience,* 95 (14), 8322-8327 (1998).
7. Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.
8. Joerg Reifart, Christoph Liebetrau, Christian Troidl, Katharina Madlener and Andreas Rolf, "Noninvasive sampling of the distal airspace via HME-filter fluid is not useful to detect SARS-CoV-2 in intubated patients," *Crit. Care* (2021) 25:126.
9. Helen Tsai, Brett S. Phinney, Gabriela Grigorean, Michelle R. Salemi, Hooman H. Rashidi, John Pepper, and Nam K. Tran, "Identification of Endogenous Peptides in Nasal Swab Transport Media used in MALDI-TOF-MS Based COVID-19 Screening," *ACS Omega* 2022, 7, 20, 17462-17471.

What is claimed is:

1. A method for detecting tuberculosis (TB) using exhaled air, the method including:

capturing truncated proteoforms in the exhaled air aerosol produced by a patient using a sample capture element including a packed bed column, wherein exhaled air is drawn into the sample capture element using a pump at a predetermined flow rate;

extracting the truncated proteoforms from the packed bed column into one or more collected liquid samples including the truncated proteoforms;

analyzing the one or more collected liquid samples using MALDI-TOFMS;

detecting the presence of TB if the truncated proteoforms includes one or more of interleukin-10 receptor subunit alpha (IL10RA), protein phosphatase 1 regulatory subunit 17 (PPR17), collagen alpha-1 (II) chain (COL2A1), collagen alpha-1 (III) chain (COL3A1), or complement component C6 (C6).

2. The method of claim 1, wherein a capture efficiency of the sample capture element for truncated proteoforms in exhaled air is greater than 99%.

3. The method of claim 1, wherein the packed bed column includes one or more of resin beads having C18 functional groups on the surface, cellulose beads having sulfate ester functional groups on the surface, or mixtures thereof.

4. The method of claim 1, wherein the packed bed column includes solid particles including one or more of resins, cellulose, silica, agarose, or hydrated $Fe_3O_4$ nanoparticles.

5. The method of claim 3, wherein the resin beads and cellulose beads have a nominal diameter of at least about 20 μm.

6. The method of claim 3, wherein the resin beads and cellulose beads have a nominal diameter of between about 40 μm and about 150 μm.

7. The method of claim 1, wherein extracting the truncated proteoforms includes flushing the packed bed column with one or more solvents and collecting the solvent including truncated proteoforms from the packed bed.

8. The method of claim 7, wherein the one or more solvents includes one or more of acetonitrile, methanol, trifluoro acetic acid (TFA), or isopropanol (IPA), the remaining being water.

9. The method of claim 7, wherein the one or more solvents includes between about 50 vol.-% and about 70 vol.-% acetonitrile in water, between about 50 vol.-% and about 70 vol.-% isopropanol in water, or between about 0.05 vol.-% TFA in water.

10. The method of claim 1, wherein the sample capture element is removably connected to an exhaled air tubing of a ventilator assisting the breathing of an intubated patient.

11. The method of claim 10, wherein the predetermined flow rate drawn through the packed bed column using the pump is between about 200 ml/min and about 3 L/min.

12. The method of claim 1, wherein the sample capture element is removably connected to a breath collection element configured to receive an individual's face, wherein the breath collection element forms a tight-fit with the individual's face.

13. The method of claim 12, wherein the breath collection element includes one or more of a CPR rescue mask, a CPAP mask, or a ventilator mask.

14. The method of claim 12, wherein the predetermined flow rate drawn through the packed bed column using the pump is between about 200 ml/min and about 600 ml/min.

15. The method of claim 12, wherein the sample capture element is removably connected to a port disposed in the breath collection element proximate to the individual's chin when the breath collection element is positioned on the individual's face without any interconnecting tubing.

* * * * *